(12) United States Patent
Nahm et al.

(10) Patent No.: US 8,011,228 B2
(45) Date of Patent: Sep. 6, 2011

(54) METHOD FOR THE DETECTION OF LATERAL FLOW ASSAY AND STRIP AND LASER-INDUCED EPIFLUORESCENCE AND COMPACT SCANNER THEREFOR

(75) Inventors: Kie-Bong Nahm, Seoul (KR); Eui-Yeol Choi, Chuncheon-si (KR); Jae-Hoon Kim, Chuncheon-si (KR)

(73) Assignees: Bio-Med Photonics, Co., Ltd., Gangwon-Do (KR); Boditechmed, Inc., Gangwon-Do (KR)

( * ) Notice: Subject to any disclaimer, the term of this patent is extended or adjusted under 35 U.S.C. 154(b) by 736 days.

(21) Appl. No.: 10/585,467

(22) PCT Filed: Jan. 5, 2005

(86) PCT No.: PCT/KR2005/000016
§ 371 (c)(1),
(2), (4) Date: Sep. 24, 2008

(87) PCT Pub. No.: WO2005/066624
PCT Pub. Date: Jul. 21, 2005

(65) Prior Publication Data
US 2009/0211345 A1    Aug. 27, 2009

(30) Foreign Application Priority Data
Jan. 5, 2004    (KR) .................. 10-2004-0000440

(51) Int. Cl.
*G01N 13/00*    (2006.01)
(52) U.S. Cl. ...................................... 73/61.55
(58) Field of Classification Search ............... 73/61.55, 73/61.48, 23.41
See application file for complete search history.

(56) References Cited

U.S. PATENT DOCUMENTS
5,658,723 A    8/1997    Oberhardt et al. .............. 435/4
(Continued)

FOREIGN PATENT DOCUMENTS
WO    WO 03/062824 A1    7/2003

OTHER PUBLICATIONS

Ceska et al, "A New and Simple Radioimmunoassay Method for the Determination of IGE," Immunochemistry, (1972) vol. 9, p. 1021.

(Continued)

*Primary Examiner* — Hezron Williams
*Assistant Examiner* — Tamiko D Bellamy
(74) *Attorney, Agent, or Firm* — Casimir Jones, S.C.

(57) ABSTRACT

Disclosed is a lateral flow quantitative assay method capable of quantitatively determining the concentration and analyzing the spatial distribution of a disease marker by employing the principle of the laser-induced fluorescence detection technique, which is based on detecting emitted fluorescence when laser light is focused to the disease marker deposited onto a lateral flow quantitative assay chip. The present invention discloses a strip, a laser-induced epifluorescence detection device and a small scanner for the assay method. The present assay method is advantageous in terms of allowing quantitative point-of-care diagnostics in hospitals, being capable of specifically detecting a disease marker by optimizing a lateral flow assay biochip for diagnosis of a specific disease, allowing more accurate quantitative analysis of analytes, and being capable of simultaneously analyzing several cancer markers, reducing the hook effect and expanding the detection range and accurately measuring concentration of analytes.

15 Claims, 12 Drawing Sheets

U.S. PATENT DOCUMENTS

| | | | |
|---|---|---|---|
| 5,705,338 A | 1/1998 | Piran et al. | 435/6 |
| 5,712,170 A | 1/1998 | Kouvonen et al. | 436/518 |
| 6,136,549 A | 10/2000 | Feistel et al. | 435/7.1 |
| 7,371,582 B2 * | 5/2008 | Nahm et al. | 436/514 |
| 7,476,549 B2 * | 1/2009 | Nahm et al. | 436/514 |

OTHER PUBLICATIONS

Lehtone et al, "Antigen Density in Elisa; Effect on Avidity Dependency," Journal of Immunological Methods, (1980) vol. 36, p. 63-70.

Lehtone et al, "Antigen Attachment in Elisa," Journal of Immunological Methods, (1980) vol. 34, p. 61-70.

Alwine et al, "Detection of Specific RNAs or Specific Fragments of DNA by Fractionation in Gels and Transfer to Diazobenzyloxymethyl Paper," Methods in Enzymology, (1979) vol. 68, p. 220.

P. Tijssen, "Practice and Theory of Enzyme Immunoassays," Elsevier (1985) vol. 15, p. 318-322.

* cited by examiner

Ag line    Test line
   No CRP

Ag line    Test line
   1-10 ug/ml CRP

STD: Mouse IgG-Reference line
AFP (alpha-fetoprotein): 15 ng/ml-Liver
CEA (carcinoma embryonic antigen): 15 ng/ml-Colorectal
CA15-3: 30 UI/ml-Breast
CA19-9: 35 UI/ml-Ovary
CA125: 40UI/ml-Uterus

METHOD FOR THE DETECTION OF LATERAL FLOW ASSAY AND STRIP AND LASER-INDUCED EPIFLUORESCENCE AND COMPACT SCANNER THEREFOR

TECHNICAL FIELD

The present invention relates to a lateral flow quantitative assay method capable of quantitatively determining the concentration and analyzing the spatial distribution of a disease marker by employing the principle of the laser-induced fluorescence detection technique, which is based on detecting emitted fluorescence when laser light is focused to the disease marker deposited onto a lateral flow quantitative assay chip, and a strip, a laser-induced epifluorescence detection device and a small scanner for the method.

BACKGROUND ART

Over the past 30 years, development of novel diagnostic apparatuses and methods which involve quantitative and qualitative analyses of extremely small quantities of substances contained in a sample taken for biopsy, such as blood or urine, has actively and rapidly progressed and even now, is still progressing at a high speed. RIA (Radioimmunological Assay) using radioactive isotopes was introduced in the 1950s, and ELISA (Enzyme Linked ImmunoSorbent Assay) was developed and advanced in the 1970s and 1980s. The ELISA method is the most popular laboratory test today and one of requisite tools for research in medical or life science fields. Recently, modified ELISA methods have been developed. Among them, for example, there is a method for analyzing a plurality of analytes at one time by immobilizing a plurality of antibodies onto a 96-well plate.

By typical immunodiagnostic methods, including RIA or ELISA, only one kind of analyte per sample can be quantified, using expensive analytical machinery and tools, while performing a multi-step procedure. Therefore, these methods cannot be readily used in a small-scale hospital, emergency room, the home, etc., where such equipments are not provided. In order to make up for this weak point, a convenient diagnostic kit using immunochromatography has been developed.

Using such diagnostic kit, it is possible to obtain a test result in 15 minutes after applying a sample such as whole blood, serum, urine, etc. to the kit. A representative type of immunochromatographic assays is a lateral flow assay. A kit for the lateral flow assay has a structure comprising a sample pad, to which a sample is applied, a releasing pad coated with a detector antibody, a developing membrane (typically, nitrocellulose) or strip, in which components of the sample move at different rates to be individually separated and to undergo antibody-antigen reaction, and an absorption pad which is provided at the far end of the sample pad to cause the sample to keep moving. The detector antibody is fixed onto, for example, colloidal gold particles to enable the detection. Latex beads or carbon particles may be used instead of gold particles. The diagnostic kit for the lateral flow assay is generally designed to detect an analyte in a sandwich configuration. Upon applying a liquid sample to the sample pad of the kit, an analyte contained in the sample begins to move from a sample pad. Firstly, the analyte reacts with a detector antibody releasably adhered to a releasing pad to form an antigen-antibody conjugate, which continues to develop in this conjugated form. Then, while moving through the developing membrane, the antigen-antibody conjugate reacts once more with a capture antibody fixed on a developing membrane to form a capture antibody-antigen-detector antibody conjugate in a sandwich form. Since the capture antibody is fixed on the developing membrane, conjugates are accumulated in the area where the capture antibodies are fixed. Proteins are invisible to the naked eye. Therefore, the presence and amount of conjugates are determined by means of an amount of gold or silver particles attached to a certain area of the developing membrane.

The lateral flow assay can be widely and conveniently used in various fields such as pregnancy diagnosis, cancer diagnosis, and microbe detection. However, since quantification cannot be performed with the naked eye and hence, an exact amount of an analyte cannot be determined, its application is restricted. Especially, when a judgment should be made around a cut-off value, it is difficult to make an exact diagnosis. For example, in case of prostate cancer, when a detected value is 3.9 ng/ml which is very close to the standard cut-off value of 4 ng/ml, an exact diagnosis cannot be made.

Immunodiagnosis is now rapidly developing, and in the near future, will be able to easily and promptly identify and analyze a sample. Therefore, we can diagnose the condition of disease. The RIA or ELISA method which can quantify an analyte at present involves several complicated steps for such quantification, including treatment with an enzyme and washing. Similarly, the conventional convenient diagnostic kits have difficulties in providing quantified results. Therefore, there is a great demand for a general assay method which can perform quantification more rapidly, conveniently and sensitively. With the method, an ordinary unskilled person can practice diagnosis or analysis in any place.

In addition, the immunoassay technology is an attractive method for qualitatively and quantitatively detecting target substances contained in biological samples using DNA chips or protein chips incorporating membranes in a short time and at low cost. Since diagnostic chips produced for such analysis selectively detect biomedical markers generated when a specific disease develops, they are very important in diagnosing a target disease and can provide information on abnormal conditions. Diagnostic chips used in such an immunoassay technology greatly simplify the conventional pathological tests with respect to time, space and procedure. However, most chips including the conventional lateral flow quantitative assay strips still allow only qualitative analysis. That is, with these chips, immunological reaction results are converted to visually identifiable forms and interpreted based on the subjective criteria of analyzers. At present, this assay is gaining popularity due to its convenience of not requiring specific analysis apparatuses. A representative example is a pregnancy diagnostic chip.

Diagnostics should be performed by precise qualitative or quantitative assays. At present, available representative analysis tools are spectrometry and fluorescence analysis, which are applied for high-throughput screening. A representative example of the fluorescence analysis is laser-induced fluorescence detection. The laser-induced fluorescence detection technique is based on exciting a fluorescent material from a ground state to an excited state using a laser light of a wavelength absorbed by the fluorescent material, and measuring the intensity of fluorescence emitted upon the return of the electronic energy state from the excited state to the ground state, whereby the measured fluorescence intensity indicates the concentration of the fluorescent material. In this way, DNA and protein samples that are tagged with fluorescent materials are quantitatively analyzable.

On the other hand, DNA chips contain DNA molecules with various lengths ranging from several hundreds to hundreds of thousands of base pairs in a very small space by That is, DNA chips are biological microchips that are capable of analyzing gene expression patterns, gene defects, protein distribution, response patterns, and the like, using DNA molecules attached to a small support made of a transparent or semi-transparent substance, such as a glass or silicon. DNA chips are classified to two categories according to the size of the genetic material attached thereonto: cDNA chips and oligonucleotide chips. A cDNA chip contains at least 500-bp or longer full-length open reading frames attached thereonto, and an oligonucleotide chip contains oligonucleotides consisting of about 15 to 25 bases.

In general, there are two types of DNA chip manufacturing technologies using target DNA molecules: direct synthesis of oligonucleotides on a support and immobilization of amplified target DNA molecules onto a support. The on-chip synthesis of DNA molecules, which is based on a photolithographic fabrication technique employed in the semiconductor chip industry, allows high density deposition of the DNA molecules, but the target DNA molecules are limited to be about 20 nucleotides in length. The photolithographic-based DNA chip manufacturing technology is suitable for disease diagnosis or single nucleotide polymorphism (SNP). The second technology is commonly applied to differential gene expression studies, and immobilizes target DNA molecules onto a slide coated with poly L-lysine, amine or aldehyde.

Protein chip fabrication techniques and applications are known to those skilled in the art and also described in many journals and patent publications. For example, a protein chip is manufactured by depositing antibodies to proteins associated with several diseases onto a small transparent or semi-transparent wafer, and can be used for early diagnosis for the presence and pathogenic states of specific diseases by being treated with an analyte, prepared using a body fluid collected from a patient, and applied to the chip as a biochemical marker. The small wafer is prepared by immobilizing a desired protein onto a common glass plate, for example, using avidin. Also, the wafer is prepared using polystyrene as a wafer substrate, and this polystyrene binds proteins with high efficiency. Polyvinylchloride and polypropylene are also used according to the nature of proteins immobilized onto a wafer.

A process of depositing proteins onto the aforementioned transparent or semi-transparent wafer is well known to those skilled in the art. For example, in case of using a polystyrene wafer, eight grooves 1 mm wide, 2 mm long and 1.5 mm deep are created in a row at intervals of 1 mm on a polystyrene wafer 1.5 cm wide and 1.5 cm long. When proteins to be analyzed are individually deposited in the grooves of the polystyrene wafer with a diameter of about 400 nm and intervals of about 500 nm, ten proteins can be deposited in a 1-cm length of the wafer. In total, about 80 proteins can be deposited onto the single wafer.

On the other hand, a confocal laser scanning system is most commonly used in detecting fluorescence using the laser-induced fluorescence detection technique. With this system using a laser as a light source, only fluorescence emerged from a single position of a specimen, among fluorescence signals emitted from the specimen, enters a photomultiplier tube by a specific photometric system, and the output from the photomultiplier tube, which is an analog electrical signal, is converted to a digital image.

That is, as shown in FIG. 10, the confocal laser scanning system uses a laser light source 11 to illuminate only a light with a proper wavelength a specimen labeled with a fluorescent material and emit fluorescence in the specimen. This system is designed to detect only fluorescence emitted from a fluorescence point by finally passing fluorescence emitted from an area several tens of micrometers containing the specimen through a pinhole 16 formed in front of an optical detector 17. The reference numerals 12, 14 and 15 indicate a spatial filter for incident light, an objective lens and the specimen, respectively.

Most fluorescence scanners employing this principle provide information on the intensity and spatial distribution of fluorescence emitted in a diagnostic chip with high precision, but have difficulties in use for point of care (POC) diagnostics, as follows. First, these kinds of scanners are supplied with a high price of 50,000 dollars, thereby making it difficult for the convenient diagnostic chips to be widely used. Also, the fluorescence scanners are not convenient products in use because they must be maintained under a stringently managed environment to execute the high sensitivity detection. These problems with the desk-top scanners can be partially overcome by employing a small-sized scanner. A small scanner called "Triage" from Biosite Diagnostics Inc. is available along with a diagnostic chip, which provides rapid quantitative measurements for cardiac markers, but is cost-ineffective because of providing high-priced diagnostics, for example, at 50,000 won per test in Korea. Response Biomedical's RAMP diagnostic system is the closest technology to the laser-induced fluorescence detection technique and fluorescence immunological cancer diagnostic devices using the technique, but is to date not commercialized.

DISCLOSURE OF THE INVENTION

Accordingly, the present invention has been made keeping in mind the above problems occurring in the prior art, and an object of the present invention is to provide a lateral flow quantitative assay method capable of quantitatively determining the concentration and analyzing the spatial distribution of a disease marker by employing the principle of the laser-induced fluorescence detection technique, which is based on detecting emitted fluorescence emitted when laser light is focused to the disease marker deposited onto a lateral flow quantitative assay chip, and a strip, a laser-induced epifluorescence detection device and a small scanner for the method.

It is another object of the present invention to provide a lateral flow quantitative assay method allowing quantitative point-of-care diagnostics in hospitals and being capable of specifically detecting a disease marker by optimizing a lateral flow assay biochip for diagnosis of a specific disease, and a strip, a laser-induced epifluorescence detection device and a small scanner for the method.

It is a further object of the present invention to provide more accurate quantitative analysis of analytes upon concentration measurement of the analytes by fluorescence immunochromatography by fixing a mouse IgG reference substance in a reference line and arranging the reference line in front of a test line.

It is a still further object of the present invention to provide a method capable of simultaneously analyzing several cancer markers by micro-arraying in a row a plurality of antibodies associated with cancer onto a developing membrane.

It is yet another object of the present invention to provide an accurate measurement of analyte concentration by establishing a window wall surface of a cartridge housing with an angle maximizing the laser light efficiency and amplification of collected light.

It is still another object of the present invention to provide a lateral flow quantitative assay method of reducing the hook effect and widening a detection range by fixing an Ag line with which Ag or a detector reacts in back of a test line, and a strip, a laser-induced epifluorescence detection device and a small scanner for the method.

It is still another object of the present invention to provide a lateral flow quantitative assay method capable of accurately measuring the concentration of analytes by applying a sample to a strip and reading the strip after a predetermined time, and a strip, a laser-induced epifluorescence detection device and a small scanner for the method.

Figure 1:
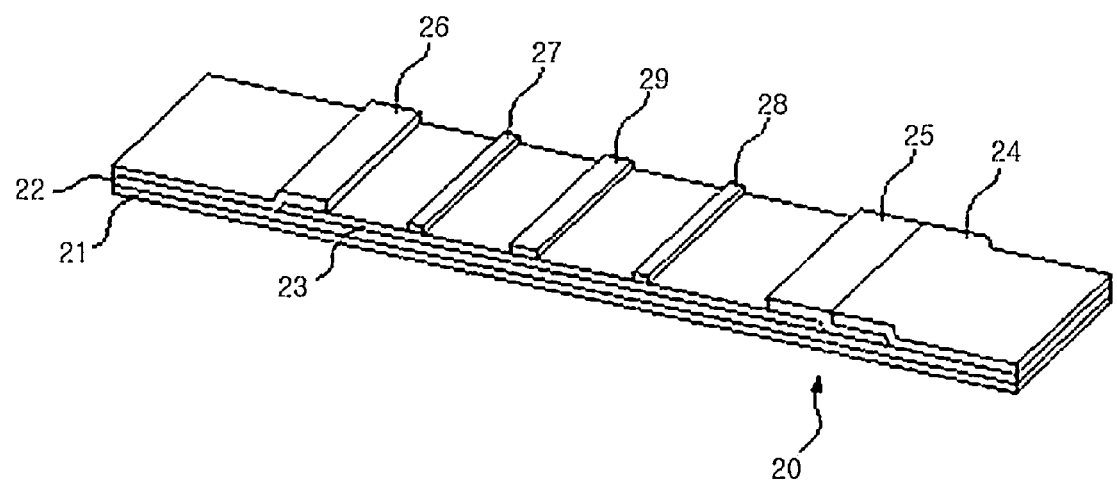
FIG. 1 is a perspective view of the conventional lateral flow quantitative assay strip.

| Explanation of Numerals | |
|---|---|
| 20. | Lateral flow quantitative assay strip |
| 21. | Backing |
| 22. | Adhesive |
| 23. | Chromatography medium |
| 24. | Sample pad |
| 25. | Conjugate releasing pad |
| 26. | Absorption pad |
| 27. | The second captor |
| 28. | The first captor |
| 29. | Test line |
| 31. | Light receiving unit |
| 32. | Analog digital converter |
| 33. | CPU |
| 34. | Transport unit |
| 35. | Position sensor |
| 36. | Input unit |
| 37. | Memory |
| 38. | Power monitor |
| 39. | Output unit |
| 40. | Display |
| 40'. | Printer |
| 41. | Exciter filter |
| 42. | Optical detector |
| 43. | Spatial filter |
| 44. | Light collecting lens |
| 45. | Fluorescent filter |
| 46. | Condenser lens |

BEST MODE FOR CARRYING OUT THE INVENTION

To accomplish the above objects, in accordance with a first aspect, the present invention provides a lateral flow quantitative assay method including: applying a liquid sample that is expected to contain an analyte to one end of a chromatography medium; migrating the liquid sample through the chromatography medium to react the analyte with a labeled detector adsorbed on a section located at a predetermined distance from the sample application site in a sample developed direction, thereby forming an analyte/labeled detector conjugate; migrating the analyte/labeled detector conjugate through the chromatography medium to react the analyte/labeled detector conjugate with an unlabeled captor that is identical to or different from the detector and immobilized on a viewing window defined around a middle portion of the chromatography medium, thereby forming a labeled detector/analyte/unlabeled captor triple conjugate in which the analyte is captured between the labeled detector and the unlabeled captor in a sandwich-like fashion; and measuring an amount of the triple conjugate to quantify the analyte in the liquid sample, wherein the method is characterized in that:

(a) the labeled detector is labeled with a fluorescent substance and reacts with the analyte in the liquid sample to form the fluorescently-labeled detector/analyte conjugate;

(b) the unlabeled captor is dispensed in lines within a viewing window on the chromatography medium and reacts with the fluorescently-labeled detector/analyte conjugate that means of a mechanical automation or electronic control, etc.

has been migrated along the chromatography medium to form the fluorescently-labeled detector/analyte/unlabeled captor triple conjugate;

(c) a reference detector, which is different from the detector and the captor and labeled with a fluorescent material identical to that used in labeling the detector and reacts with a reference material in the liquid sample, is adsorbed on the section of the chromatography medium where the fluorescently-labeled detector is adsorbed, and an unlabeled reference captor that reacts with the fluorescently-labeled reference detector is dispensed and immobilized in double reference lines in front of the viewing window on the chromatography medium to provide a reference conjugate of fluorescently-labeled reference detector/reference material/unlabeled reference captor as the liquid sample passes through the chromatography medium; and (d) an amount of the analytes is determined by passing a laser presented from a shape control lens for laser beam through an exciter filter, irradiating the filtered light to the epifluorescence medium containing the triple analyte conjugate and the reference conjugate, passing light reflected from the epifluorescence medium through a collection lens to form parallel light, passing the parallel light through a fluorescent filter to remove scattered incident light and presenting only a pure fluorescence component to a condenser lens to focus the pure fluorescence component to a center of a pinhole, removing light except for the parallel light at the pinhole, presenting the parallel light to an optical detector, transmitting the incident parallel light to a CPU via an analog digital converter (ADC), and comparing a fluorescence intensity of the triple analyte conjugate with a reference fluorescence intensity of the reference conjugate to quantify the analyte.

In accordance with a second aspect, the present invention provides a lateral flow quantitative assay strip, including: a backing; a sample pad adhered to one end of the backing and to which a liquid sample is applied; a conjugate releasing pad adhered to the backing in such a way that one end of the sample pad, close to an opposite end of the backing, overlaps with an end of the conjugate releasing pad to which a labeled detector is releasably attached to react with an analyte in the liquid sample to form a conjugate; a chromatography medium adhered to the backing in such a way that one end of the medium overlaps with an end of the conjugate releasing pad, close to an opposite end of the backing, and on which a captor is immobilized, which is identical to or different from the detector and reacts with and captures a conjugate released from the conjugate releasing pad as the sample develops to form a sandwich type conjugate; and an absorption pad to absorb the sample developing along the chromatography medium and to absorb and remove unreacted labeled substances, wherein the strip is characterized in that:

the detector releasably attached to the conjugate releasing pad is labeled with a fluorescent material;

a reference detector that is labeled with a fluorescent material identical to that used in labeling the detector and reacts with a reference material in the liquid sample is further releasably attached to the conjugate releasing pad;

the captor is dispensed and immobilized in lines within a viewing window on the chromatography medium, and an unlabeled reference captor that is different from the detector and the captor is dispensed and immobilized in double reference lines in front of the viewing window on the chromatography medium, to form a conjugate of fluorescently-labeled detector/analyte/unlabeled captor and a reference conjugate of fluorescently-labeled reference detector/reference material/unlabeled reference captor as the liquid sample passes through the chromatography medium; and an amount of the analyte is determined by passing a laser presented from a laser beam shape control lens through an exciter filter, irradiating the filtered light to the epifluorescence medium containing the triple analyte conjugate and the reference conjugate, passing light reflected from the epifluorescence medium through a collection lens to form parallel light, passing the parallel light through a fluorescent filter to remove scattered incident light and presenting only a pure fluorescence component to a condenser lens to focus the pure fluorescence component to a center of a pinhole, removing light except for the parallel light at the pinhole, presenting the parallel light to an optical detector, transmitting the incident parallel light to a CPU via an analog digital converter (ADC), and comparing a fluorescence intensity of the triple analyte conjugate with a reference fluorescence intensity of the reference conjugate to quantify the analyte.

In accordance with a third aspect, the present invention provides a small scanner for quantitative analysis of an analyte, which is integrated with a laser-induced epifluorescence detection device into a single body, wherein the laser-induced epifluorescence detection device includes:

(i) a strip comprising: a backing; a sample pad adhered to one end of the backing and to which a liquid sample is applied; a conjugate releasing pad adhered to the backing in such a way that one end of the sample pad, close to an opposite end of the backing, overlaps with an end of the conjugate releasing pad to which a labeled detector is releasably attached to react with an analyte in the liquid sample to form a conjugate; a chromatography medium adhered to the backing in such a way that one end of the medium overlaps with an end of the conjugate releasing pad, close to an opposite end of the backing, and on which a captor is immobilized, which is identical to or different from the detector and reacts with and captures a conjugate released from the conjugate releasing pad as the sample develops to form a sandwich type conjugate; and an absorption pad to absorb the sample developing along the chromatography medium and to absorb and remove unreacted labeled substances, wherein the strip is characterized in that:

the detector releasably attached to the conjugate releasing pad is labeled with a fluorescent material;

a reference detector that is labeled with a fluorescent material identical to that used in labeling the detector and reacts with a reference material in the liquid sample is further releasably attached to the conjugate releasing pad;

the captor is dispensed and immobilized in lines within a viewing window on the chromatography medium; and an unlabeled reference captor that is different from the detector and the captor is dispensed and immobilized in double reference lines in front of the viewing window on the chromatography medium;

(ii) a cartridge to install therein the strip, the cartridge including a sample loading inlet and a window having a sloped wall surface, which are formed on a top plate of a cartridge housing; and (iii) a laser, a shape control lens for laser beam, an exciter filter, a collection lens, a fluorescent filter, a condenser lens, a spatial filter, an optical detector, an analog digital converter (ADC) and a CPU, wherein the components of the detection device are arranged in a structure such that a laser presented from a lens for control of shape of a laser beam of the laser is passed through an exciter filter, the filtered light is irradiated to an epifluorescence medium containing a conjugate of fluorescently-labeled detector/analyte/unlabeled captor and formed in the viewing window and a reference conjugate of fluorescently-labeled reference detector/reference material/unlabeled reference captor formed in the reference line as the liquid sample passes through the chromatography medium of the strip, light reflected from the epifluorescence medium is passed through a collection lens to form parallel light, the parallel light is passed through a fluorescent filter to remove scattered incident light, only a pure fluorescence component is presented to a condenser lens to focus the pure fluorescence component to a center of a pinhole, light except for the parallel light is removed at the pinhole, the parallel light is presented to an optical detector, and the incident parallel light is transmitted to CPU via an analog digital converter (ADC), wherein the small scanner allows the detection device to determine an amount of the analyte in the sample by comparing a fluorescence intensity of the triple analyte conjugate with a reference fluorescence intensity of the reference conjugate.

In one aspect to accomplish the above objects, the present invention provides a lateral flow quantitative assay method including: applying a liquid sample that is expected to contain an analyte to one end of a chromatography medium; migrating the liquid sample through the chromatography medium to react the analyte with a labeled detector adsorbed on a section located at a predetermined distance from the sample application site in a sample developed direction, thereby forming an analyte/labeled detector conjugate; migrating the analyte/labeled detector conjugate through the chromatography medium to react the analyte/labeled detector conjugate with an unlabeled captor that is identical to or different from the detector and immobilized on a viewing window defined around a middle portion of the chromatography medium, thereby forming a labeled detector/analyte/unlabeled captor triple conjugate in which the analyte is captured between the labeled detector and the unlabeled captor in a sandwich-like fashion; and measuring an amount of the triple conjugate to quantify the analyte in the liquid sample, wherein the method is characterized in that:

(a) the labeled detector is labeled with a fluorescent substance and reacts with the analyte in the liquid sample to form the fluorescently-labeled detector/analyte conjugate;

(b) the unlabeled captor is dispensed in lines within a viewing window on the chromatography medium and reacts with the fluorescently-labeled detector/analyte conjugate that has been migrated along the chromatography medium to form the fluorescently-labeled detector/analyte/unlabeled captor triple conjugate;

(c) a reference detector, which is different from the detector and the captor and labeled with a fluorescent material identical to that used in labeling the detector and reacts with a reference material in the liquid sample, is adsorbed on the section of the chromatography medium where the fluorescently-labeled detector is adsorbed, and an unlabeled reference captor that reacts with the fluorescently-labeled reference detector is dispensed and immobilized in double reference lines in front of the viewing window on the chromatography medium to provide a reference conjugate of fluorescently-labeled reference detector/reference material/unlabeled reference captor as the liquid sample passes through the chromatography medium; and (d) an amount of the analytes is determined by passing a laser presented from a shape control lens for laser beam through an exciter filter, irradiating the filtered light to the epifluorescence medium containing the triple analyte conjugate and the reference conjugate, passing light reflected from the epifluorescence medium through a collection lens to form parallel light, passing the parallel light through a fluorescent filter to remove scattered incident light and presenting only a pure fluorescence component to a condenser lens to focus the pure fluorescence component to a center of a pinhole, removing light except for the parallel light at the pinhole, presenting the parallel light to an optical detector, transmitting the incident parallel light to a CPU via an analog digital converter (ADC), and comparing a fluorescence intensity of the triple analyte conjugate with a reference fluorescence intensity of the reference conjugate to quantify the analyte.

In another aspect to accomplish the above objects, the present invention provides a lateral flow quantitative assay strip, including: a backing; a sample pad adhered to one end of the backing and to which a liquid sample is applied; a conjugate releasing pad adhered to the backing in such a way that one end of the sample pad, close to an opposite end of the backing, overlaps with an end of the conjugate releasing pad to which a labeled detector is releasably attached to react with an analyte in the liquid sample to form a conjugate; a chromatography medium adhered to the backing in such a way that one end of the medium overlaps with an end of the conjugate releasing pad, close to an opposite end of the backing, and on which a captor is immobilized, which is identical to or different from the detector and reacts with and captures a conjugate released from the conjugate releasing pad as the sample develops to form a sandwich type conjugate; and an absorption pad to absorb the sample developing along the chromatography medium and to absorb and remove unreacted labeled substances, wherein the strip is characterized in that:

the detector releasably attached to the conjugate releasing pad is labeled with a fluorescent material;

a reference detector that is labeled with a fluorescent material identical to that used in labeling the detector and reacts with a reference material in the liquid sample is further releasably attached to the conjugate releasing pad;

the captor is dispensed and immobilized in lines within a viewing window on the chromatography medium, and an unlabeled reference captor that is different from the detector and the captor is dispensed and immobilized in double reference lines in front of the viewing window on the chromatography medium, to form a conjugate of fluorescently-labeled detector/analyte/unlabeled captor and a reference conjugate of fluorescently-labeled reference detector/reference material/unlabeled reference captor as the liquid sample passes through the chromatography medium; and an amount of the analyte is determined by passing a laser presented from a laser beam shape control lens through an exciter filter, irradiating the filtered light to the epifluorescence medium containing the triple analyte conjugate and the reference conjugate, passing light reflected from the epifluorescence medium through a collection lens to form parallel light, passing the parallel light through a fluorescent filter to remove scattered incident light and presenting only a pure fluorescence component to a condenser lens to focus the pure fluorescence component to a center of a pinhole, removing light except for the parallel light at the pinhole, presenting the parallel light to an optical detector, transmitting the incident parallel light to a CPU via an analog digital converter (ADC), and comparing a fluorescence intensity of the triple analyte conjugate with a reference fluorescence intensity of the reference conjugate to quantify the analyte.

In a further aspect to accomplish the above objects, the present invention provides a compact scanner for quantitative analysis of an analyte, which is integrated with a laser-induced epifluorescence detection device into a single body, wherein the laser-induced epifluorescence detection device includes:

(i) a strip comprising: a backing; a sample pad adhered to one end of the backing and to which a liquid sample is applied; a conjugate releasing pad adhered to the backing in such a way that one end of the sample pad, close to an opposite end of the backing, overlaps with an end of the conjugate releasing pad to which a labeled detector is releasably attached to react with an analyte in the liquid sample to form a conjugate; a chromatography medium adhered to the backing in such a way that one end of the medium overlaps with an end of the conjugate releasing pad, close to an opposite end of the backing, and on which a captor is immobilized, which is identical to or different from the detector and reacts with and captures a conjugate released from the conjugate releasing pad as the sample develops to form a sandwich type conjugate; and an absorption pad to absorb the sample developing along the chromatography medium and to absorb and remove unreacted labeled substances, wherein the strip is characterized in that:

the detector releasably attached to the conjugate releasing pad is labeled with a fluorescent material;

a reference detector that is labeled with a fluorescent material identical to that used in labeling the detector and reacts with a reference material in the liquid sample is further releasably attached to the conjugate releasing pad;

the captor is dispensed and immobilized in lines within a viewing window on the chromatography medium; and an unlabeled reference captor that is different from the detector and the captor is dispensed and immobilized in double reference lines in front of the viewing window on the chromatography medium;

(ii) a cartridge to install therein the strip, the cartridge including a sample loading inlet and a window having a sloped wall surface, which are formed on a top plate of a cartridge housing; and (iii) a laser, a shape control lens for laser beam, an exciter filter, a collection lens, a fluorescent filter, a condenser lens, a spatial filter, an optical detector, an analog digital converter (ADC) and a CPU, wherein the components of the detection device are arranged in a structure such that a laser presented from a lens for control of shape of a laser beam of the laser is passed through an exciter filter, the filtered light is irradiated to an epifluorescence medium containing a conjugate of fluorescently-labeled detector/analyte/unlabeled captor formed in the viewing window and a reference conjugate of fluorescently-labeled reference detector/reference material/unlabeled reference captor formed in the reference line as the liquid sample passes through the chromatography medium of the strip, light reflected from the epifluorescence medium is passed through a collection lens to form parallel light, the parallel light is passed through a fluorescent filter to remove scattered incident light, only a pure fluorescence component is presented to a condenser lens to focus the pure fluorescence component to a center of a pinhole, light except for the parallel light is removed at the pinhole, the parallel light is presented to an optical detector, and the incident parallel light is transmitted to CPU via an analog digital converter (ADC), wherein the compact scanner allows the detection device to determine an amount of the analyte in the sample by comparing a fluorescence intensity of the triple analyte conjugate with a reference fluorescence intensity of the reference conjugate.

The term "sensitivity" as used herein refers to a minimum quantity of a conjugate of a captor, detector and analyte which can be detected.

The term "epifluorescence" as used herein refers to the fluorescence emitted from a conjugate of fluorescently-labeled detector/analyte/captor and/or a reference conjugate of fluorescently-labeled reference detector/reference material/reference captor, which are fixed in a viewing window and a reference line, respectively, of the lateral flow assay strip by chromatography.

The term "analyte" as used here in refers to a compound or composition being analyzed in a liquid sample. The samples which are usable in the present invention may be selected from any samples containing such an analyte. Examples include physiological fluid such as urine, serum, plasma, blood, saliva, spinal fluid, ocular liquid, amniotic fluid, etc., food such as milk and wine, chemical treatment stream such as domestic waste water. Analytes that can be examined in the present invention are largely classified into a complete antigen and a hapten (incomplete antigen). The complete antigen refers to an antigenic substance which itself has the ability to induce antibody production (immunogenicity), and mainly includes peptide hormones having high molecular weights. The hapten (incomplete antigen) refers a material which can bind to an antibody but has no ability to induce antibody production by itself, and includes peptides having relatively low molecular weights (molecular weights of about 1,000 or less). Haptens acquire the ability to induce antibody production when bound to a protein such as bovine serum albumin.

For the purposes of the present invention, examples of the complete antigens are described below, but are not limited thereto:

(1) Examples of Peptide Hormones
1) Pituitary hormones such as growth hormone (GH), adrenocorticotropic hormone (ACTH), melanocyte-stimulating hormone (MSH), prolactin, thyroid-stimulating hormone (TSH), luteinizing hormone (LH), follicle-stimulating hormone (FSH) and oxytocin;
2) Calcium metabolic regulatory hormones such as calcitonin and parathyroid hormone;
3) Insulin, proinsulin and pancreatic hormone;
4) Alimentary canal hormones such as gastrin and secretin;
5) Hormones which act on blood vessels such as angiotensin and bradykinin; and
6) Placental hormones such as human chorionic gonadotropin (hCG) and human placental lactogen (hPL).

(2) Examples of Other Substances
1) Enzymes such as prostatic acidic phosphatase (PAP), prostate-specific antigen (PSA), alkaline phosphatase, transaminase, lactic acid dehydrogenase (LDH), transaminase, trypsin and pepsinogen;
2) Cancer-specific substances such as α-fetoprotein (AFP) and cancer embryonic antigen (CEA);
3) Serum protein components such as immunoglobulin G (IgG), fibrin-fibrinogen decomposition products (FDP, D-dimer), antithrombin III (ATIII) and transferrin; and
4) Substances such as rheumatoid factor, serotonin, urokinase, ferritin and substance P.

For the purposes of the present invention, examples of haptens are described below, but are not limited thereto:

(1) Steroidal Haptens
1) Estrogens such as estrone, estradiol, estriol, estetrol, equilin and equilenin;
2) Natural or synthetic luteohormones such as progesterone, pregnanediol, pregnanetriol, 19-norethisterone and chloromadinone acetate;
3) Male sex hormones such as testosterone, dehydroepiandrosterone, dihydrotestosterone, androsterone and etiocholanorone;
4) Adrenal cortical hormones such as cortisol, cortisone, deoxycorticosterone, aldosterone and tetrahydrocortisol; and 5) Vitamins D, cholesterol, cholic acid, deoxycholic acid and chenocholic acid, and other steroids such as cardiotonic steroid, saponin and sapogenin.

(2) Physiologically active amines
1) Catecholamines such as epinephrine, norepinephrine, dopamine and ephedrine, and metabolites thereof;
2) Physiologically active alkaloids such as morphine, codeine, heroin, morphine chloride, cocaine, mescaline, papaverine, narcotine, yohimbine, reserpine, ergotamine and strychnine; and
3) Amino group-containing psychotropics such as LSD, amphetamine, methamphetamine and meprobamate.

(4) Other Examples
1) Low-molecular-weight peptides having no antigenicity such as TRH and LH-RH;
2) Thyroid hormones such as diiodothyronine, triiodothyronine and thyroxine;
3) Prostaglandins such as prostaglandin E2, prostaglandin E3 and prostaglandin F1a;
4) Vitamins such as vitamin A, B vitamins (vitamins B1, B2, B6 and B12, and the like), vitamin E and vitamin K;
5) Antibiotics such as penicillin, actinomycin, chloromycetin and tetracycline; and
6) Other in vivo components, and drugs administered into organisms and metabolites thereof.

According to the present invention, the analytes are characterized by being monoepitopic ligand or polyepitopic ligand. The polyepitopic ligand analytes will normally be poly(amino acids) i.e. polypeptides and proteins, polysaccharides, nucleic acids, and combinations thereof. Such combinations of assemblages include bacteria, viruses, chromosomes, genes, mitochondria, nuclei, cell membranes, and the like. For the most part, the polyepitopic ligand analytes employed in the present invention will have a molecular weight of at least about 5,000, more usually at least about 10,000. In the poly(amino acid) category, the poly(amino acids) of interest will generally be from about 5,000 to 5,000,000 in molecular weight, more usually from about 20,000 to 1,000,000 in molecular weight, and among the hormones of interest, the molecular weights will usually range from about 5,000 to 60,000.

The wide variety of proteins may be classified into families of proteins having similar structural features, proteins having particular biological functions, proteins related to specific microorganisms, particularly disease causing microorganisms, etc. For cells and viruses, histocompatability antigens or surface antigens will frequently be of interest.

The proteins related by structure are classified into protamines, histones, albumins, globulins, scleroproteins, phosphoproteins, mucoproteins, chromoproteins, lipoproteins, nucleoproteins, glycoproteins, and proteoglycans. In addition, unclassified proteins, for example, somatotropin, prolactin, insulin, pepsin and the like may be included. All of these proteins can be quantified by the package comprising the lateral flow assay strip and the laser-induced epifluorescence detecting apparatus according to the present invention.

A number of proteins found in human plasma which are clinically important can also be quantified by the package comprising the lateral flow assay strip and the laser-induced epifluorescence detecting apparatus according to the present invention. Examples of such plasma proteins include prealbumin, albumin, $\alpha_1$-lipoprotein, $\alpha_1$-acid glycoprotein, $\alpha_1$-antitrypsin, $\alpha_1$-glycoprotein, transcortin, 4.6S-postalbumin, tryptophan-poor $\alpha_1$-glycoprotein, $\alpha_1$X-glycoprotein, thyroxin-binding globulin, inter-$\alpha$-trypsin-inhibitor, Gc-globulin (Gc 1-1, Gc 2-1 and Gc 2-2), haptoglobin (Hp 1-1, Hp 2-1 and Hp 2-2), ceruloplasmin, cholinesterase, $\alpha_2$-lipoprotein(s), myoglobin, C-reactive protein, $\alpha_2$-macroglobulin, $\alpha_2$-HS-glycoprotein, Zn-$\alpha_2$-glycoprotein, $\alpha_2$-neuramino-glycoprotein, erythropoietin $\beta$-lipoprotein, transferrin, hemopexin, fibrinogen, plasminogen $\beta_2$-glycoprotein I and $\beta_2$-glycoprotein II, immunoglobulin G (IgG), A (IgA), M (IgM), D (IgD), E (IgE) and the like.

Other examples of analytes which can be quantified by the small scanner comprising the lateral flow assay strip and the laser-induced epifluorescence detecting apparatus according to the present invention are complement factors and blood clotting factors. Examples of the complement factors include C'1, C'1q, C'1r, C'1s, C'2, C'3 ($\beta_1$A and $\alpha_2$D), C'4, C'5, C'6, C'7, C'8 and C'9. Important blood clotting factors include fibrinogen, prothrombin, thrombin, tissue thromboplastin, proaccelerin, globulin (accelerator of proaccelerin), antihemophilic globulin (AHG), Christmas factor (plasma thromboplastin component (PTC)), Stuart-Prower factor (autoprothrombin III), plasma thromboplastin antecedent (PTA), Hagemann factor and fibrin-stabilizing factor.

Important protein hormones which can be quantified by the small scanner according to the present invention include, but are not limited to, peptide and protein hormones such as parathyroid hormone (parathromone), thyrocalcitonin, insulin, glucagons, relaxin, erythropoietin, melanotropin, somatotropin (growth hormone), corticotropin, thyrotropin, follicle-stimulating hormone, luteinizing hormone, luteomammotropic hormone and gonadotropin (chorionic gonadotropin); tissue hormones such as secretin, gastrin, angiotensin I and II, bradykinin and human placental lactogen; peptide hormones from the neurohypophysis such as oxytocin, vasopressin, and releasing factors (RF) (CRF, LRF, TRF, somatotropin-RF, GRF, FSH-RF, PIF, MIF).

Still other analytes which can be quantified by the small scanner according to the present invention include antigenic polysaccharides derived from microorganisms. Examples of the antigenic polysaccharides derived from microorganisms include, but are not limited to hemosensitins found in *Streptococcus pyogenes* polysaccharide, *Diplococcus pneumoniae* polysaccharide, *Neisseria meningitidis* polysaccharide, *Neisseria gonorrheae* polysaccharide, *Corynebacterium diphtheriae* polysaccharide, *Actinobacillus mallei* crude extract, *Francisella tularensis* lipopolysaccharide and polysaccharide, *Pasteurella pestis* polysaccharide, *Pasteurella multocida* capsular antigen, *Brucella abortus* crude extract, *Haemophilus influenzae* polysaccharide, *Haemophilus pertussis* crude extract, *Treponema reiteri* polysaccharide, *Veillonella* lipopolysaccharide, *Erysipelothrix* polysaccharide, *Listeria monocytogenes* polysaccharide, *Chromobacterium* lipopolysaccharide, *Mycobacterium tuberculosis* saline extract of 90% phenol-extracted mycobacteria and polysaccharide fraction, *Klebsiella aerogenes* polysaccharide, *Klebsiella cloacae* polysaccharide, *Salmonella typhosa* liposaccharide and polysaccharide, *Salmonella typhimurium* polysaccharide, *Shigella dysenteriae* polysaccharide, *Shigella flexneri* and *Shigella sonnei* crude extract and polysaccharide, Rickettsiae crude extract, *Candida albicans* polysaccharide and *Entamoeba histolytica* crude extract.

The microorganisms which are assayed using the package according to the present invention may be intact, lysed, ground or otherwise fragmented. Examples of such microorganisms include *Corynebacteria, Corynebacterium diptheriae*, Pneumococci, *Diplococcus pneumoniae*, Streptococci, *Streptococcus pyogenes, Streptococcus salivarus*, Staphylococci, *Staphylococcus aureus, Staphylococcus albus*, Neisseriae, *Neisseria meningitides, Neisseria gonorrheae*, Enterobacteriaciae, *Escherichia coli, Aerobacter aerogenes, Klebsiella pneumoniae, Salmonella typhosa, Salmonella* choleraesuis, Salmonella typhimurium, Shigella dysenteriae, Shigella schmitzii, Shigella arabinotarda, Shigella flexneri, Shigella boydii, Shigella Sonnei, Proteus vulgaris, Proteus mirabilis, Proteus morgani, Pseudomonas aeruginosa, Alcaligenes faecalis, Vibrio cholerae, Hemophilus influenzae, Hemophilus ducreyi, Hemophilus hemophilus, Hemophilus aegypticus, Hemophilus parainfluenzae, Bordetella pertussis, Pasteurella pestis, Pasteurella tulareusis, Brucella melitensis, Brucella abortus, Brucella suis, Bacillus anthracis, Bacillus subtilis, Bacillus megaterium, Bacillus cereus, Clostridium tetani, Clostridium perfringens, Clostridium novyi, Clostridium septicum, Clostridium histolyticum, Clostridium tertium, Clostridium bifermentans, Clostridium sporogenes, Mycobacterium tuberculosis hominis, Mycobacterium bovis, Mycobacterium avium, Mycobacterium leprae, Mycobacterium paratuberculosis, Actinomyces israelii, Actinomyces bovis, Actinomyces naeslundii, Nocardia asteroids, Nocardia brasiliensis, Spirochetes, Treponema pallidum Spirillum minus, Treponema pertenue Streptobacillus, Treponema carateum, Borrelia recurrentis, Leptospira icterohemorrhagiae, Leptospira canicola, Mycoplasmas, Mycoplasma pneumoniae, Listeria monocytogenes, Erysipelothrix rhusiopathiae, Streptobacillus moniliformis, Donvania granulonatis, Bartonella bacilliformis, Rickettsia prowazekii, Rickettsia mooseri, Rickettsia rickettsii, Rickettsia conori, Rickettsia australis, Rickettsia sibiricus, Rickettsia akari, Rickettsia tsutsugamushi, Rickettsia burnetii, Rickettsia Quintana, Chlamydia, Cryptococcus neoformans, Blastomyces dermatidis, Histoplasma capsulatum, Coccidioides immitis, Paracoccidioides brasiliensis, Candida albicans, Aspergillus fumigatus, Mucor corymbifer (Absidia corymbifera), Rhizopus oryzae, Rhizopus arrhizus, Rhizopus nigricans, Sporotrichum schenkii, Fonsecaea pedrosoi, Fonsecaea compacta, Fonsecae dermatidis, Cladosporium carrionii, Phialophora verrucosa, Aspergillus nidulans, Madurella mycetomi, Madurella grisea, Allescheria boydii, Phialosphora jeansilmei, Microsporum gypseum, Trichophyton mentagrophytes, Keratinomyces ajelloi, Microsporum canis, Trichophyton rubrum, Microsporum adnouini, Adenoviruses, Herpes Viruses, Herpes simplex, Varicella, Herpes Zoster, Cytomegalovirus, Pox Viruses, Variola, Vaccinia, Poxvirus bovis, Paravaccinia, Molluscum contagiosum, Picaornaviruses, Poliovirus, Coxsackievirus, Echoviruses, Rhinoviruses, Myxoviruses, Influenza (A, B, and C), Parainfluenza (1-4), Mumps Virus, Newcastle Disease Virus, Measles Virus, Rinderpest Virus, Canine Distemper Virus, Respiratory Syncytial Virus, Rubella Virus, Arboviruses, Eastern Equine Eucephalitis Virus, Western Equine Eucephalitis virus, Sindbis Virus, Chikugunya Virus, Semliki Forest Virus, Mayora Virus, St. Louis Encephalitis Virus, California Encephalitis Virus, Colorado Tick Fever Virus, Yellow Fever Virus, Dengue Virus, Reovirus Types 1-3, Hepatitis A Virus, Hepatitis B Virus, Tumor Viruses, Rauscher Leukemia Virus, Gross Virus, Maloney Leukemia Virus, Epstein Barr Virus, and other parasites related to diseases such as Dog Heart Worm (microfilaria), Malaria, Schistosomiasis, Coccidosis and Trichinosis.

The monoepitopic ligand analytes which can be quantified using the small scanner of the present invention will generally have a molecular weight from about 100 to 2,000, more usually from 125 to 1,000. Representative examples of the analytes include drugs, metabolites, pesticides, pollutants, and the like. Included among drugs are the alkaloids. Among the alkaloids are morphine alkaloids, for example morphine, codeine, heroin, dextromethorphan, their derivatives and metabolites; cocaine alkaloids, for example cocaine and benzoyl ecgonine, their derivatives and metabolites; ergot alkaloids, for example the diethylamide of lysergic acid; steroid alkaloids; iminazoyl alkaloids; quinazoline alkaloids, insoquinoline alkaloids; quinoline alkaloids, for example quinine and quinidine; diterpene alkaloids; and their derivatives and metabolites.

Also, drugs of steroids can be quantified by the small scanner of the present invention. Specific examples thereof include estrogens, androgens, andrenocortical steroids, bile acids, cardiotonic glycosides and aglycones, for example digoxin and digoxigenin, saponins and sapogenins, their derivatives and metabolites. Further included are the steroid mimetic substances, such as diethylstilbestrol. Another group of drugs which can be quantified by the package of the present invention is lactams having from 5 to 6 annular members, which include the barbiturates, for example, phenobarbital and secobarbital, diphenylhydantonin, primidone, ethosuximide, and metabolites thereof. The next group of drugs is aminoalkylbenzenes, in which the alkyl group has from 2 to 3 carbon atoms. Examples include the amphetamines, catecholamines such as ephedrine, L-dopa, epinephrine, narceine, papaverine, and metabolites thereof. The next group of drugs is benzheterocyclics, for example oxazepam, chlorpromazine, tegretol, imipramine, and derivatives and metabolites thereof, in which the heterocyclic rings are azepines, diazepines and phenothiazines. The next group of drugs is purines, for example theophylline, caffeine, and metabolites and derivatives thereof. The next group of drugs includes those derived from marijuana, for example cannabinol and tetrahydrocannabinol. The next group of drugs includes the vitamins such as A, B, for example $B_{12}$, C, D, E and K, folic acid, and thiamine. The next group of drugs is prostaglandins, which differ by the degree and sites of hydroxylation and unsaturation. The next group of drugs is antibiotics, for example, penicillin, chloromycetin, antinomycetin, tetracycline, terramycin, and metabolites and derivatives thereof. The next group of drugs is the nucleosides and nucleotides, for example, ATP, NAD, FM, adenosine, guanosine, thymidine, and cytidine with their appropriate sugar and phosphate substituents. The next group of drugs is miscellaneous individual drugs, for example, methadone, meprobamate, serotonin, meperidine, amitriptyline, nortriptyline, lidocaine, procaineamide, acetylprocaineamide, propranolol, griseofulvin, valproic acid, butyrophenones, antihistamines, anticholinergic drugs, such as atropine, and metabolites and derivatives thereof. Metabolites related to conditions of disease include spermine, galactose, phenylpyruvic acid and porphyrin Type 1. The next group of drugs is aminoglycosides, such as gentamicin, kanamicin, tobramycin, and amikacin.

The analytes which can be quantified by the small scanner of the present invention also include pesticides. Their examples are polyhalogenated biphenyls, phosphate esters, thiophosphates, carbamates, polyhalogenated sulfenamides, metabolites and derivatives thereof.

The analytes which can be quantified by the small scanner of the present invention further include receptor analytes, whose molecular weights will generally range from 10,000 to $2\times10^8$, more usually from 10,000 to $10^6$. For immunoglobulins, IgA, IgG, IgE and IgM, the molecular weights will generally vary from about 160,000 to about $10^6$. Enzymes will normally range from about 10,000 to 1,000,000 in molecular weight. Natural receptors vary widely, generally being at least about 25,000 molecular weight and may have a molecular weight of 106 or higher, including such materials as avidin, DNA, RNA, thyroxine binding globulin, thyroxine binding prealbumin, transcortin, etc.

In addition to the above-described analytes, the small scanner of the present invention may be used to quantify tumor markers, angiogenesis related markers, cardiac markers, Alzheimer disease related markers, cancer related genes, environmental toxins, abused drugs and the like. As examples of the tumor markers, alpha 1-acid glycoprotein, CEA, AFP, PSA/free PSA, CA 15-3, CA 19-9, CA 27-9, CA-50, CA 125, CA 72-4, calcitonin, elastase-1, ferritin, pepsinogen I, PIVKA II, Procollagen III peptide, beta HCG, beta 2-microglobulin, neuron specific enolase, CYFRA 21-1 (Cytokeratin 19), Secretin, NMP (nuclear matrix protein), COX-1, TPA (Tissue Polypeptide, Antigen) and the like may be included. The angiogenesis related markers include angiogenic factors and angiostatic factors. Specific examples of the angiogenic factors include aFGF (acidic Fibroblast Growth Factor), bFGF (basic Fibroblast Growth Factor), VEGF (Vascular Endothelial Growth Factor), angiogenin, angiopoietin 1, heparinase, scatter factor, HGF (Hepatocyte Growth Factor), PDGF (Platelet Derived Growth Factor), Pleiotrophin, TGF α, TGF β, IL-8, TNF α, and prostagladins E1 and E2. Specific examples of the angiostatic factors include endostatin, angiostatin, cartilage-derived inhibitor, heparinase, angiopoietin2, IFN α, IFN β, IFN γ, platelet factor 4, 16 kDa prolactin fragment, protamine, thrombospandin, TIMPs (Tissue Inhibitor of Metalloproteinase), thalidomide and TNP 470 (Fumagilin analogue). Examples of the cardiac markers include creatin kinase-BB, creatin kinase-MB, creatin kinase-MM, myoglobin, MLC (Myosin Light Chain), troponin I, troponin C, troponin ITC, troponin T, CRP and FABP (Fatty Acid Binding Protein). Examples of the Alzheimer disease related markers include glutamine synthetase, melano transferrin and β-amyloid protein. Examples of the cancer related gene include bcl-2, C-erbB-2, C-myc, CSF-1 receptor, EGF receptor, H-ras, K-ras (p12), L-myc, mdr-1, N-myc, N-ras, p53 exon 4, p53 exon 5, p53 exon 6, p53 exon 7, p53 exon 8, p53 exon 9, TcR-α, TcR-β, TcR-γ and TcR-δ. The environmental toxins include for example, microcystin, dioxin and PCB. Examples of the abused drugs include amphetamines, barbiturates, benzodiazepin, cannabinoids, cocaine, morphine, phencyclidine and TBPE.

According to the present invention, the useful fluorescent material by which, an analyte sample is labeled, may have a difference of 20 nm or more between its absorption wavelength and emission wavelength. Representative examples of the fluorescent material include, but are not limited to, fluorescent particles, quantum dots, lanthanide chelates, such as samarium (Sm), Europium (Eu) and Terbium (Tb), and fluorescence, such as FITC, Rhodamine green, thiadicarbocyanine, Cy2, Cy3, Cy5, Cy5.5, Alexa 488, Alexa 546, Alexa 594 and Alexa 647). Preferred fluorescent materials which can be used in detection of DNA are Cy3 and Cy5. In general, the fluorescence intensity is directly proportional to the intensity of excitation light.

According to the present invention, the labeling material binds to the detector which specifically binds to an analyte via a linker. Such linkers include, but are not limited to, N-[k-Maleimidoundecanoyloxy])-sulfosuccinimide ester (sulfo-KMUS), succinimidyl-4-(N-maleimidomethyl)-cyclohexane-1-carboxy[6-Amidocaproate] (LC-SMCC), N—K-maleimidoundecanoic acid (KMUA), succinimidyl-4-[p-maleimidophenyl]butyrate (SMBP), succinimidyl-6-[(β-maleimido-propionamido)hexanoate] (SMPH), Succininidyl-4-[N-maleimidomethyl]cyclohexane-1-carboxylate (SMCC), sulfosuccinimidyl-4-[N-maleimidomethyl]cyclohexane-1-carboxylate (sulfo-SMCC), N-succinimidyl[4-iodoacetyl]aminobenzoate (SIAB), sulfosuccinimidyl(4-iodoacetyl)aminobenzoate (sulfo-siab), N-[γ-maleimidobutyryloxy]sulfo-succininimide ester (sulfo-GMBS), N-[γmaleimidobutyryloxy]succininimide ester (GMBS), succinimidyl 3-[bromoacetamido]propionate (SBAP), N-β-maleimidopropionic acid (BMPA), N-[α-maleimidoacetoxy]succinimide ester (AMAS), N-succinimidyl S-acetylthiopropionate (SATP), m-maleimidobenzoyl-N-hydroxysuccinimide ester (MBS), m-maleimidobenzoyl-N-hydroxysulfosuccinimide ester (sulfo-MBS), N-e-maleimidocapric acid (EMCA), N-[e-maleimidocaproyloxy]succinimide ester (EMCS), N-succinimidyl-[4-vinylsulfonyl]benzoate (SVSB), N-[β-maleimidopropyloxy]succinimide ester (BMPS) and 1-ethyl-3-[3-dimethylaminopropyl]carbodiimide hydrochloride (EDC). These linkers will react with thiol groups of the detector.

The lateral flow assay strip of the present invention may take a shape of a rectangle, circle, oval, triangle and other various shapes, provided that there should be at least one direction along which a test solution moves by capillarity. In case of an oval or circular shape, in which the test solution is initially applied to the center thereof, there are different flow directions. However, what is taken into consideration is that the test solution should move in at least one direction toward a predetermined position. Thickness of the strip according to the present invention is usually 0.1 to 2 mm, more usually 0.15 to 1 mm, preferably 0.2 to 0.7 mm, though it is not important. In general, a minimum thickness is determined depending on a strength of the strip material and needs for producing a readily detectable signal while, a maximum thickness is determined depending on handling ease and cost of reagents. In order to maintain reagents and provide a sample of a defined size, the strip is constructed to have a relatively narrow width, usually less than 20 mm, preferably less than 10 mm. In general, the width of the strip should be at least about 1.0 mm, typically in a range of about 2 mm to 12 mm, preferably in a range of about 4 mm to 8 mm. The length of the strip is determined considering kinds of analytes, the number of test lines or spots and the number of reference lines on the chromatography medium, space between pads, convenience of handling and the like. Usually, it is 1 to 40 cm, preferably about 2 to 25 cm, more preferably about 4 to 20 cm. However, the strip can be practically prepared to have any length.

Solvents for a liquid sample to be analyzed are commonly aqueous media, which include oxidizing solvents having usually 1 to 6 carbon atoms, more usually 1 to 4 carbon atoms containing about 40 wt % or less of another polar solvent, particularly alcohol, ether, etc. In common, a cosolvent is contained in an amount of less than about 20 wt %. Under some circumstances according to the nature of an analyte, a part or all of the aqueous medium can be provided by the analyte per se.

The aqueous medium has pH of typically 4 to 11, more typically 5 to 10, preferably 6 to 9. The pH is selected in accordance with critical binding affinity sites of the binding elements and ability to maintain voluntary generation of signals by a signal generation system. Various buffers can be used to adjust pH to a desired level and maintain pH at that level during an assay. Representative buffers include for example, borate, phosphate, carbonate, Tris, and barbital. Though usable buffers are not particularly important, a certain buffer can be preferred for individual assays as opposed to other buffers. Also, a non-ionic detergent can be preferably added to the sample in an amount of about 0.05 to 0.5 wt %. In addition, a variety of polyoxyalkylene compounds of about 200 to 20,000 Daltons can be used.

Typically, the assay is carried out at a mild temperature and preferably, is carried out at a substantially constant temperature. A suitable temperature for generating assay signal is usually about 4° C. to 50° C., more usually about 10° C. to 40° C., frequently ambient temperature, i.e. about 15° C. to 25° C.

The concentration of the analyte to be analyzed in a subject solution is typically about $10^{-4}$ to about $10^{-15}$ M, more typically about $10^{-6}$ to $10^{-14}$ M. The concentrations of other reagents is commonly determined considering the concentration of a desired analyte and protocol.

In general, concentrations of various reagents in a sample and reagent solution are determined in accordance with a concentration range of a target analyte and a final concentration of each reagent is determined empirically to optimize the sensitivity of the assay within a target range. Each reagent can be used in an excess amount along with a certain protocol, as long as it does not lower the sensitivity of the assay.

Now, the small scanner integratedly formed of the lateral flow assay strip and the laser-induced epifluorescence detecting apparatus will be explained in detail.

Backing of the Lateral Flow Assay Strip

The backing is typically made of water-insoluble, non-porous and rigid material and has a length and width equal to the pads situated thereon, along which the sample develops, but may have a dimension being less or greater than the pad. In preparation of the backing, various natural and synthetic organic and inorganic materials can be used, provided that the backing prepared from the material should not hinder capillary actions of the absorption material, nor non-specifically bind to an analyte, nor interfere with the reaction of the analyte with a detector. Representative examples of polymers usable in the present invention include, but are not limited to, polyethylene, polyester, polypropylene, poly(4-methylbutene), polystyrene, polymethacrylate, poly(ethylene terephthalate), nylon, poly(vinyl butyrate), glass, ceramic, metal and the like.

On the backing, a variety of pads are adhered by means of adhesives. Proper selection of adhesives may improve the performance of the strip and lengthen the shelf life of the strip. According to the present invention, pressure-sensitive adhesives (PSA) may be representatively used in the lateral flow assay strip. Typically, the adhesion of different pads of the lateral flow assay strip is accomplished as the adhesive penetrates into pores of the pads, thereby binding pads together with the backing. With respect to such binding, ability of an adhesive to flow under normal conditions is referred to as "cold flow". Since no heat is applied when coating PSA on to the pad, cold flow of a certain level is indispensable for binding between the pad and the backing. If the level of cold flow is too low, the initial binding force is low, causing insufficient binding between the pad and the backing. In contrast, if the level of cold flow is too high, the adhesive migrates to the pads with which it is bound during storage of the strip, thereby clogging the pores, forming hydrophobic stains or leading to problems of redamping the pad. Such problems associated with the cold flow of the adhesive can be solved by using a direct-casting membrane. For example, in the direct-casting membrane, a supporting plastic sheet prevents the adhesive from entering pores of the membrane and thus vertical migration of the adhesive is prevented during storage.

Sample Pad of the Lateral Flow Assay Strip

The sample pad basically acts to receive the fluid sample containing an analyte. Other than this function, the sample pad may have a function to filter insoluble particles in the sample. From this point of view, preferred sample pads of the present invention are composed of cellulose filter paper or glass fiber filter paper capable of providing the filtering function. Usually, a cellulose membrane (grade 903) produced by S & S is used.

Preferably, the sample pad is treated in advance to prevent the analyte in the sample from being non-specifically adsorbed thereto, to allow the components of the sample to readily migrate through the chromatography medium, to maintain the sensitivity of the reaction and to prevent undesirable nonspecific reactions which may occur between the labeled detector and components of the sample. The pretreatment of the sample pad is generally performed by treating the pad with an inactive protein or surfactant. For instance, the pretreatment is carried out by immersing the pad material in a solution of 0.1 to 10% bovine serum albumin (BSA)-containing 0.1 M Tris buffer solution (pH 6-9), a solution of 0.1% to 10% skim milk powder in 0.1 M Tris buffer solution (pH 6-9) and/or 0.1 to 10% casein solution. After leaving the sample pad as it is at 37° C. for 1 hour or at 4° C. for 1 day, the sample pad is removed from the solution and washed with a Tris buffer solution and dried. The pretreatment with a surfactant is carried out by immersing the pad in for example, 0.01% to 1% solution of Triton X-100 or Tween 20, non-ionic surfactant, followed by drying. Preferably, the sample pad may be treated with an inactive protein and then a surfactant. However, these pretreatment steps are determined in accordance with kinds of analytes and samples.

Conjugate Releasing Pad of the Lateral Flow Assay Strip

On the conjugate releasing pad of the lateral flow assay strip according to the present invention, a fluorescently-labeled detector capable of reacting with an analyte in the sample to form a conjugate is adhered but is not immobilized. Since the detector is releasably attached, when forming a conjugate via reaction with an analyte in the sample, it can move together with the sample through the chromatography medium.

It is preferred for material of the conjugate releasing pad to have a rapid filtering speed and a good ability to hold particles. As such material, synthetic material such as polyester and glass fiber filter can be used. Commonly, glass fiber and polyester produced by S & S are used. Since these are biologically inactive and have more delicate fibrous material than natural material, they are not distorted or swollen when an aqueous reagent or sample is applied. Preferably, the conjugate releasing pad is pretreated with a reagent such as a surfactant so that an analyte is prevented from non-specifically binding to the fluorescently-labeled detector on the releasing pad and the conjugate can smoothly be released and migrate.

Methods for attaching a reagent onto the conjugate releasing pad include an impregnation process in which a pad such as glass fiber is immersed in a solution of a high density reagent particularly formulated, followed by drying. However, the impregnation process has several simple problems. Firstly, the pad can be crumpled or distorted during dehydration. Secondly, during drying the pad in a oven, reagents may be separated from the pad or reconstituted due to surface tension and gravimetric action according to location on the pad. Thirdly, chemical changes of reagents may take place with the passage of time in the immersion bath, causing the reagents to have different adsorption rates, whereby the reagents are unevenly coated on the pad. One method to minimize these problems is to perform drying of the pad in an oven at less than 40° C. for several hours. Another method is to lyophilize the pad instead of drying the pad in an oven. Such lyophilization is preferred to drying in the oven in that stability of the detector can be secured.

As an alternative method to the impregnation process, a dispensing process may be used. This process involves dispensing 12 to 15 μl of a reagent solution per cm of the pad using a dispenser and drying it. The drying of the pad is carried out the same as in the impregnation process. Also, the pad may be lyophilized.

Furthermore, the conjugate releasing pad may be treated with a stabilizing agent and shielding agent. Examples of the stabilizing agent include saccharides such as sucrose, trehalose, etc. Examples of the shielding agent include proteins such as BSA (Bovine Serum Albumin), gelatin, casein, skim milk and the like, but are not limited thereto.

Chromatography Medium of the Lateral Flow Assay Strip

The material of the chromatography medium may be any one that can allow the fluid sample and conjugate to rapidly move via capillary action to reach the captor immobilized thereon and preferably has homogeneous properties. Typically, the chromatography medium refers to a porous material having a pore diameter of at least 0.1µ, preferably 1.0µ and through which an aqueous medium can readily move via capillary action. Such material generally may be hydrophilic or hydrophobic, including for example, inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly(vinyl chloride), polyacrylamide, cross-linked dextran, agarose, polyacrylate, etc.; either used by themselves or in conjunction with other materials. Also, ceramics may be used. The chromatography medium can be bound to the backing. Alternatively, the chromatography may be the backing per se. The chromatography medium may be multifunctional or be modified to be multifunctional to covalently bind to the captor.

When using a high concentration of the captor chemically binding to the chromatography medium so as to react and trap the analyte/detector conjugate migrating from the conjugate releasing pad, preferably, an activated filter paper sheet is used as the chromatography medium. When a CNBr activated cellulose is selected as the material for the filter paper, an activated cellulose filter paper sheet can be easily prepared by a known method such as the method described by Ceska and Lundkvist (Immunochemistry, 9, 1021 (1972)) and Lehtone and Viljanen (J. Immunol. Methods. 36,63 (1980) and 34,61 (1980)). When the material is DBM activated cellulose, it can be easily prepared by a known method such as the method described by Alwine (Methods Enzymol., 68, 220 (1979)). Further, a commercially available activated nylon film (Pall Immunodyne, USA) may also be used.

One of the important properties of the chromatography medium is its capacity to immobilize a captor. Such binding capacity is varied depending upon a pore structure of the medium and a post-treatment which the medium undergose. A preferred chromatography medium which can be used in the present invention is a nitrocellulose (NC) membrane and examples thereof are described in Table 1 below.

TABLE 1

| Supplier | Product | Sec/4 cm (flow rate[a]) | IgG/cm$^{2[b]}$ |
|---|---|---|---|
| S&S (without a backing) | AE 98 | 160-210 | 20-30 ug |
|  | AE 99 | 120-160 | 20-30 ug |
| Millipore (with a backing bound) | AE 100 | 90-120 | 20-30 ug |
|  | HF 090 | 80-100 | >95 |
|  | HF 120 | 107-133 | >95 |
|  | HF 135 | 120-150 | >95 |

TABLE 1-continued

| Supplier | Product | Sec/4 cm (flow rate[a]) | IgG/cm$^{2[b]}$ |
|---|---|---|---|
|  | HF 180 | 160-200 | >95 |
|  | HF 240 | 214-266 | >120 |
| Sartorius (with a backing bound) | CN 90 | 88-94 | 10-30 |
|  | CN 140 | 137-153 | 10-30 |
|  | CN 200 | 205-233 | 10-30 |

[a]time for distilled water to move on the medium by 4 cm
[b]maximum binding capacity of IgG per cm$^2$ In the table, the most preferred membrane is CN 90 membrane. This membrane has the smallest variation in flow rate among the described products. The binding capacity on the order of 10 to 30 ug is sufficient since amplification of fluorescent substances is excellent.

The captors are immobilized on the chromatography medium via chemical bonding. The chemical bonding is carried out according to a known method (LABORATORY TECHNIQUES IN BIOCHEMISTRY AND MOLECULAR BIOLOGY, Volume 15, Edited by R. H. BURDON and P. H. Van KNIPPENBERG ELSEVIER AMSTERDAM: NEW YORK, OXFORD (1985) P. 318-322). Further, the captor may be bound to the activated paper sheet through a second substance (ex. antibody protein, etc.). When the second substance present therebetween is an antibody (to be referred to as "second antibody" hereinafter), and for example, when the captor to be fixed is a monoclonal antibody derived from mouse, there may be used the activated paper sheet to which an excess of anti-mouse γG (gamma globulin) hetero-animal antibody is bound and then a proper amount of the captor is bound by an immunoreaction. When the substance present therebetween is a protein, for example, there may be used the activated paper sheet to which an excess of protein A is bonded and then a proper amount of the trapping antibody is bound.

In order to uniformly wet test lines within the viewing window on the chromatography medium, a blocking technique is used. By blocking the chromatography medium with a material which can enhance rewetting of the chromatography medium, it is guaranteed that the medium can be rewetted uniformly and rapidly. There are four kinds of blocking material: proteins such as BSA and gelatin; surfactants such as SDS, Tween 20 and Triton X-100; polymers such as PVA, PEG and PVP. These blocking materials can be used at three points. Firstly, they can be applied directly onto the chromatography medium. This method can provide highly uniform rewetting effects. However, the blocking should be performed after immobilization of the captors but before adhesion of the sample pad. This method requires use of expensive coating equipments. Also, the captors should be redissolved and moreover, the blocking material may deteriorate the antigenicities and storage life of the captors. Secondly, the blocking material may be incorporated into the sample pad or conjugate releasing pad. This method has merits in that it can be readily performed at low cost and re-dissolution of the captors is not needed, but its blocking effect is not satisfactory. This method is preferable in terms of easiness of handling though it has a blocking efficiency inferior to the first method. Thirdly, the blocking material can be added to a buffer solution to apply the captor on to the chromatography medium. This method also has merits in that it can be readily performed at low cost and re-dissolution of the captors is not needed.

However, it has disadvantages that the captors tend to diffuse away, the antigenicities and storage life of the captors may be lowered due to the addition of the blocking agent.

In order to prevent non-specific binding of the reagents used in the sample pad, conjugate releasing pad and chromatography medium, two types of methods may be used. One is to immerse the chromatography medium to which the captors have been applied in a solution containing proteins or a highly polar polymer (e.g., polyvinyl alcohol) or to spray such a solution to the chromatography medium to block up the non-specific binding sites on the chromatography medium. However, this method may cause substitution of captors, particularly when the captors are not optimally immobilized by complete drying before the blocking step. The other method is to add a blocking agent to the sample pad. In this case, the blocking agent does not, at least initially, interfere with the binding of captors to the chromatography medium. When the liquid sample is applied to the sample pad, the blocking agent is resolubilized in the sample pad and moves together with the sample. Ideally, a sufficient amount of a blocking agent is added to the sample pad to block all non-specific bindings of all the analytes and detectors.

Figure 17:
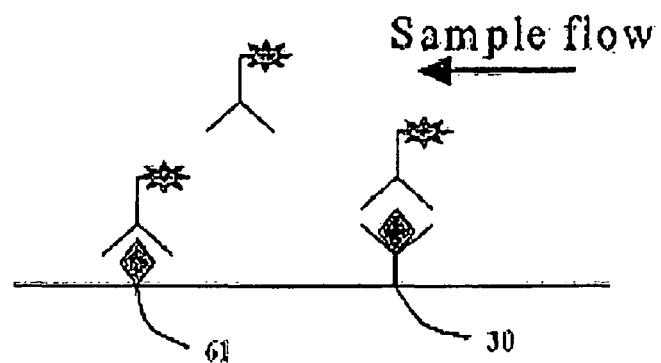
FIG. 17 shows a sample flow of the strip in case of fixing an Ag line with which Ag or a detector reacts in back of the test line and the amount of Ag is normal at a state of being mixed with a detector.

According to the preferred embodiment of the present invention, biotin-avidin conjugate is used as an analyte capture system. That is, avidin is added onto and immobilized on the test line of the strip instead of a captor (ex. antibody or antigen protein). Biotin is attached to the captor. As the biotin binds to the avidin, the captor can be automatically detected on the test line of the strip. When the captor is a protein, the binding of the biotin to the captor is effected by reacting with an amine group of lysine or arginine among amino acids. Thus, the biotin is specifically bonded to a certain site of the protein via an amine group of such amino acids. The protein with biotin attached specifically binds to the avidin which has been planted and immobilized on the strip and always maintains one orientation. Further, since the captor is not fixed via adsorption, the protein of the captor is not changed in structure or functions thereof. For these reasons, unlike the conventional method by which the captor is immobilized non-specifically on the layer of the strip without maintaining a particular orientation, according to the biotin-avidin method, the captor protein can be immobilized in one direction, and thereafter always maintain the orientation. Also, since the proteins of the captors are not changed in their structure or functions by the adsorption, they can more effectively react with the analytes in the test sample. Therefore, the biotin-avidin method can exhibit much higher sensitivity at the same concentration of an analyte compared to the conventional method. Even when an analyte is present at a concentration 10 to 100 times lower than the immobilized captor in the conventional method, a high sensitivity can be attained. Further, with an avidin-immobilized strip, when a different analyte is examined, there is no need for preparing a new strip of a different type. Only different protein-biotin conjugates and protein-fluorescently labeled conjugates as detectors are needed to assay various analytes. The method according to the present invention can be performed using a strip having the conjugate pad as in the conventional method, but also can be performed by directly adding analytes, protein-biotin conjugates, and protein-fluorescent conjugates in a solution to the sample pad without a conjugate pad. FIG. 17 shows the schematic diagram of the method using the biotin-avidin system on the test line of the strip and the conventional method.

Absorption Pad of the Lateral Flow Assay Strip

The absorption pad is means for physically absorbing the sample which has chromatographically moved through the chromatography medium via capillary action and for removing unreacted substances. Thus, the absorption pad is located at the end of the lateral flow assay strip to control and promote movement of samples and reagents and acts as a pump and container for accommodating them. The speeds of samples and reagents may vary depending on the quality and size of the absorption pad. Commonly used absorption pads are formed of water-absorbing material such as cellulose filter paper, non-woven fabric, cloth, or cellulose acetate.

Now, the lateral flow assay strip according to the present invention will be more concretely described while referring to the appended figures. From this description, the features and advantages of the present invention will become more apparent.

Figure 2:
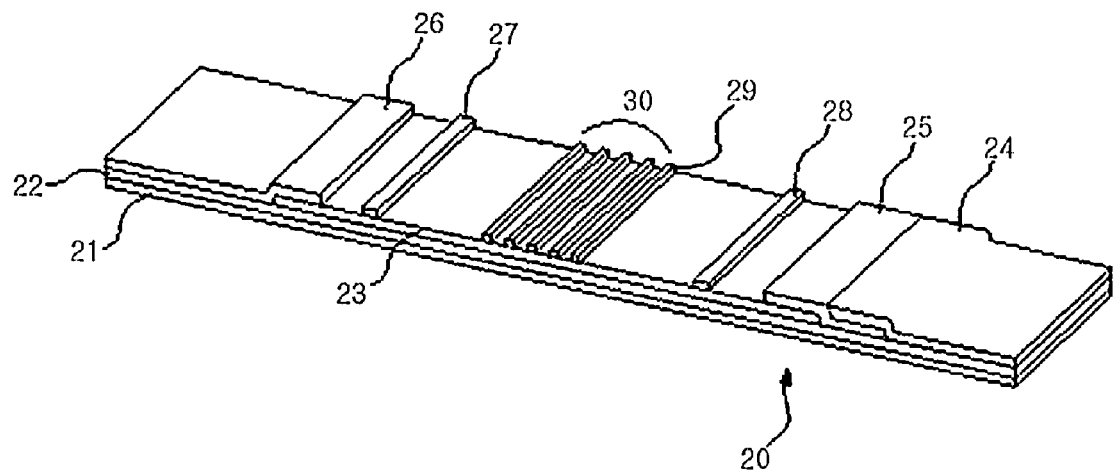
FIG. 2 is a perspective view of another conventional lateral flow quantitative assay strip.
Figure 3:
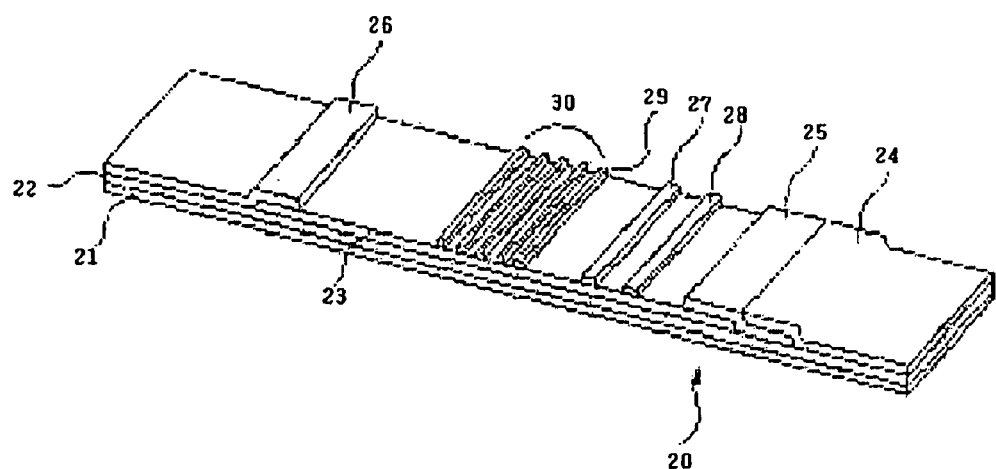
FIG. 3 is a perspective view of the lateral flow quantitative assay strip of an embodiment according to the present invention.
Figure 4:
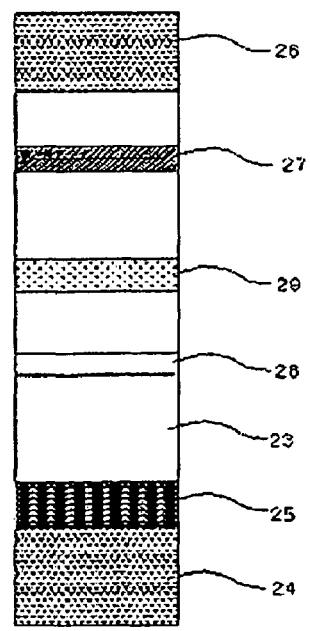
FIG. 4 is a plan view of the conventional lateral flow quantitative assay strip shown in FIG. 1.
Figure 5:
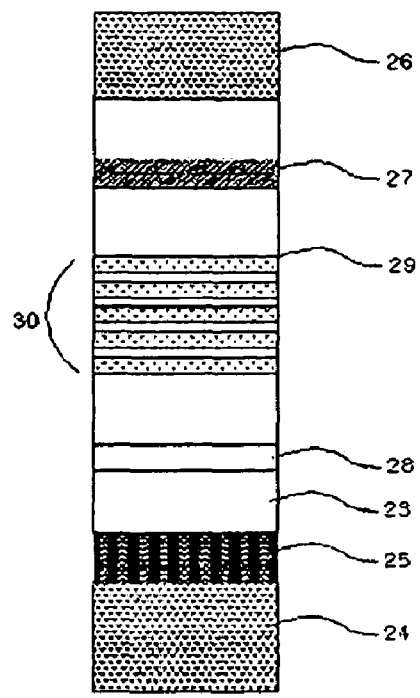
FIG. 5 is a plan view of another conventional lateral flow quantitative assay strip shown in FIG. 2.
Figure 6:
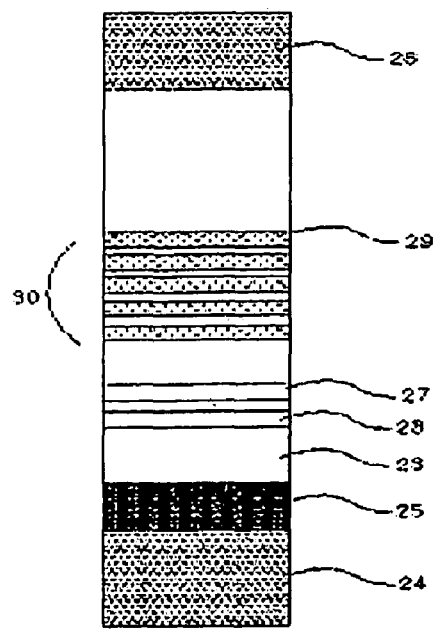
FIG. 6 is a plan view of the lateral flow quantitative assay strip of the embodiment according to the present invention shown in FIG. 3.
Figure 7:
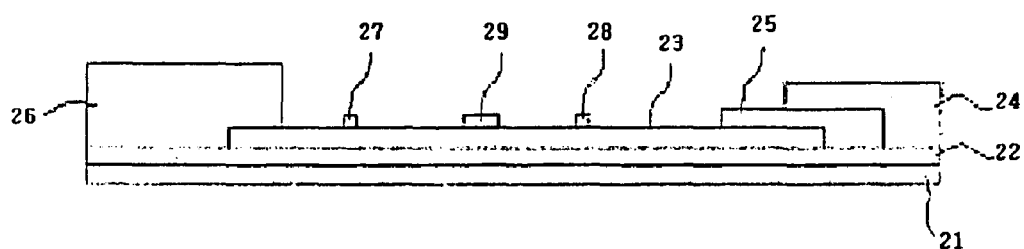
FIG. 7 is a side view of the conventional lateral flow quantitative assay strip of the shown in FIG. 1.
Figure 8:
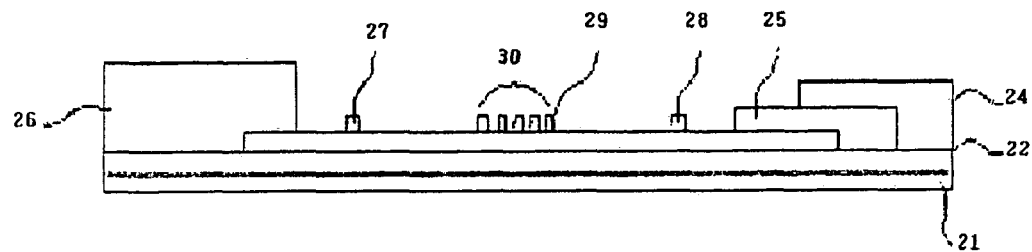
FIG. 8 is a side view of the another conventional lateral flow quantitative assay strip of the shown in FIG. 2.
Figure 9:
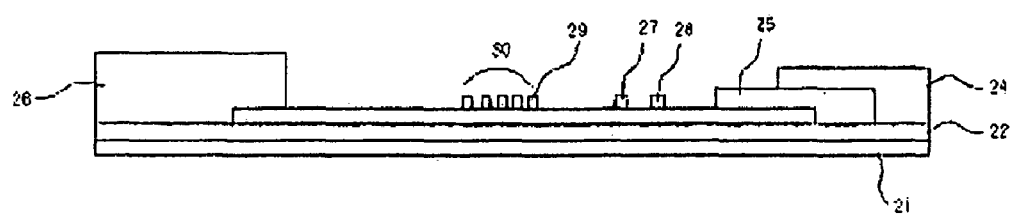
FIG. 9 is a side view of a lateral flow quantitative assay strip of the embodiment according to the present invention shown in FIG. 3.
Figure 10:
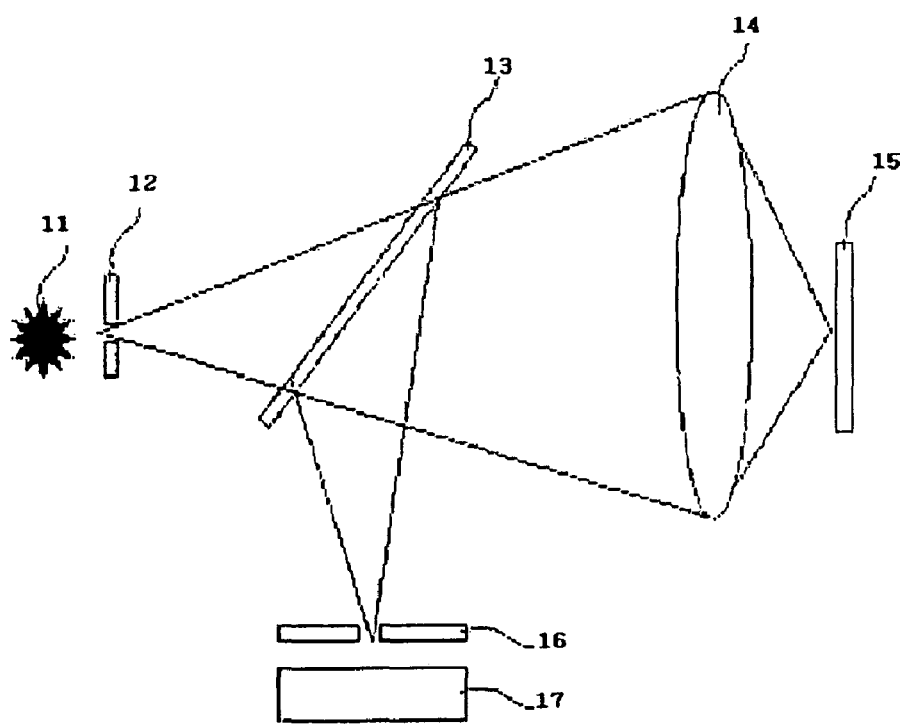
FIG. 10 is a side view illustrating a structure of a conventional laser-induced epifluorescence detector.

FIG. 1 and FIG. 2 show the conventional lateral flow assay strip. Referring to FIG. 1, the lateral flow assay strip 20 includes a sample pad 24 attached to one end of a backing 21 via an adhesion layer, upon which a liquid sample containing an analyte is applied, and successively, a conjugate releasing pad 25, a chromatography medium 23 and an absorption pad 26 toward the opposite end of the sample pad. On the conjugate releasing pad 25, a labeled detector is releasably attached so that the analyte in the liquid sample chromatographically moving via capillary action can react with the detector to form conjugate. On the chromatography medium 23, a captor which is identical to or different from the detector is immobilized in a line (test line) 29 by chemical bonding. The captor in the line 29 chemically reacts with the liquid sample and the conjugate formed on the conjugate releasing pad 25, which have been chromatographically moving on the strip, trapping the conjugate to form a labeled detector/analyte/captor conjugate. Remaining unreacted substances and the liquid sample continuously move by capillary action on the strip and are absorbed by the absorption pad 26. The amount of the analyte is determined by measuring the amount of the conjugate. The amount of the conjugate is determined as a relative value by comparing a luminescent intensity of the conjugate trapped on the chromatography medium with a reference luminescent intensity which is obtained from a conjugate formed of a reference detector which has been labeled identically with the analyte detector, and is different from the analyte detector and captor, and a reference captor which is not labeled and is different from the reference detector.

As described above, the conventional lateral flow assay strip is designed with the intention of quantitatively analyzing only one kind of an analyte in a biological sample.

FIGS. 3 to 9 show a lateral flow assay strip according to an embodiment of the present invention.

The lateral flow assay strip has a construction in which three to five kinds of detectors are releasably attached onto the conjugate releasing pad 25, and various captors in the same number as the kinds of the detectors are selected from among AFP, CEA, CA15-3, CA19-9 and CA125 and immobilized in lines on a viewing window to make it possible to simultaneously assay three to five analytes.

In the present invention, an analyte is quantitatively analyzed by measuring an intensity of epifluorescence using a laser-induced epifluorescence detection device including a laser, a shape control lens for laser beam, an exciter filter, a collection lens, a fluorescent filter, a condenser lens, a spatial filter, an optical detector, an analog digital converter (ADC) and a CPU, wherein the components of the detection device are arranged in a structure such that a laser presented from a lens for control of shape of a laser beam of the laser is passed through an exciter filter, the filtered light is irradiated to an epifluorescence medium containing a conjugate of fluorescently-labeled detector/analyte/unlabeled captor and formed in the viewing window and a reference conjugate of fluorescently-labeled reference detector/reference material/unlabeled reference captor formed in the reference line as the liquid sample passes through the chromatography medium of the strip, light reflected from the epifluorescence medium is passed through a collection lens to form parallel light, the parallel light is passed through a fluorescent filter to remove scattered incident light, only a pure fluorescence component is presented to a condenser lens to focus the pure fluorescence component to a center of a pinhole, light except for the parallel light is removed at the pinhole, the parallel light is presented to an optical detector, and the incident parallel light is transmitted to CPU via an analog digital converter (ADC).

Representative examples of the laser useful in the laser-induced epifluorescence detection device of the present invention include He—Ne lasers and diode lasers. The He—Ne lasers are exemplified by an accurate and small portable iodine-stabilized He—Ne laser (Model NEO-92SI) developed by cooperation of the National Research Laboratory of Metrology (NRLM), the Agency of Industrial Science and Technology (AIST) and the Ministry of International Trade and Industry (MITI), and model 05 LYR 173, produced by the Melles Griot (Irvine, Calif.). The diode-laser is more accurate and compact than the He—Ne laser, and is selected from various diode lasers with emission wavelengths extending from the far-infrared to the blue range of the spectrum.

The laser-induced epifluorescence detection device used in the present invention, as described above, includes a laser, a shape control lens for laser beam, an exciter filter, a collection lens, a fluorescent filter, a condenser lens, a spatial filter, an optical detector, an analog digital converter (ADC) and a CPU. Now, the principle of collecting epifluorescence by such construction will be explained in detail referring to FIGS. 11 and 12.

Figure 11:
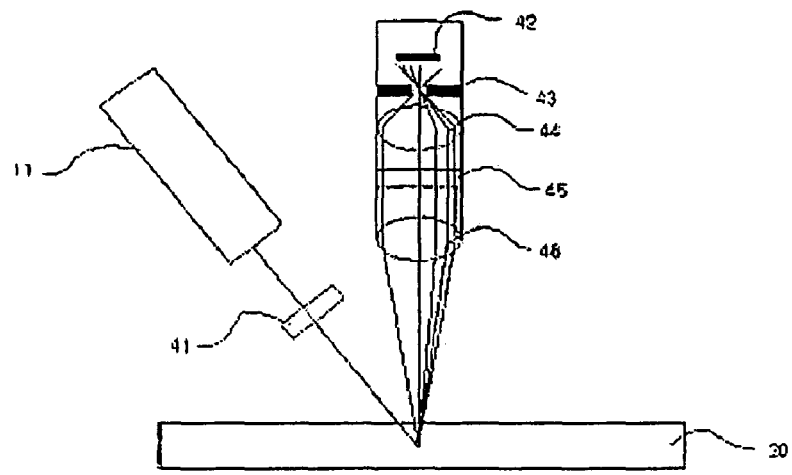
FIG. 11 is a side view illustrating a structure of a laser-induced epifluorescence detector of the embodiment according to the present invention.
Figure 12:
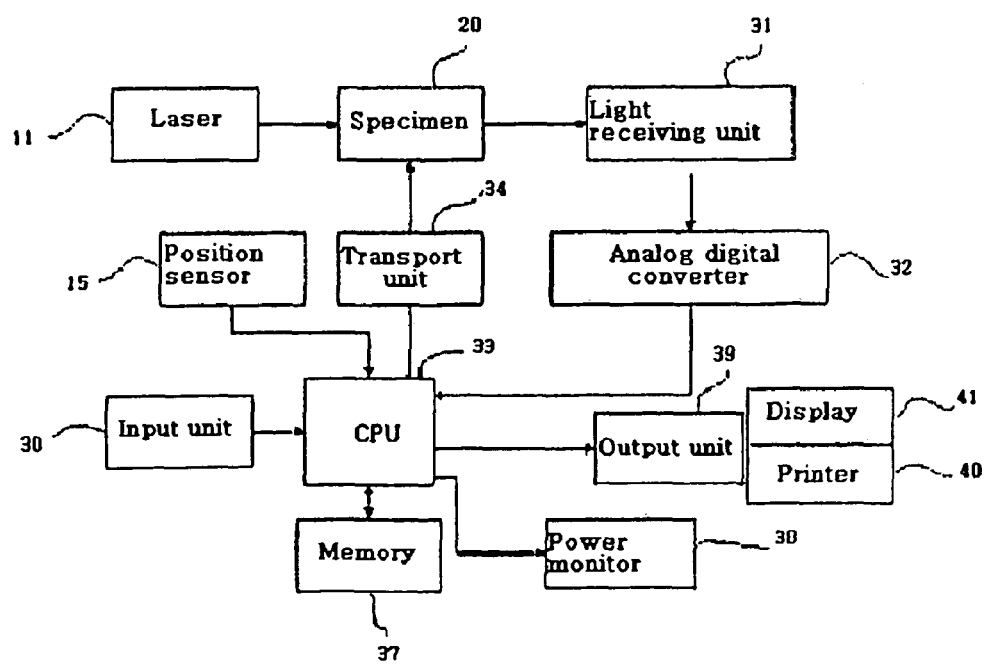
FIG. 12 is a circuit block diagram of a compact scanner according to a preferred embodiment of the present invention.

As shown in FIGS. 11 and 12, the laser-induced epifluorescence detection device of the present invention is operated, as follows. Light emitted from a laser light source 11 is processed into a point of light or a linear shape by a shape control lens for laser beam (not shown), passes through an excitation filter 41, and is illuminated to a predetermined position of a sample 20. A fluorescent substance attached to a target material placed in the illuminated position of the sample absorbs the laser energy and emits fluorescence. The fluorescence and the scattered light pass through a collection lens 46 to form parallel light. The parallel light passes through a fluorescent filter 45 to remove scattered light, and subsequently, pure fluorescence components enter a condenser lens 44. By the condenser lens 44, the pure fluorescence components are focused to a center of a spatial filter 43. In the spatial filter 43, light except for the parallel light is removed. The parallel light enters an optical detector 42. A digital signal converted by an analog digital converter (ADC) connected to the optical detector 42, that is, an electrical signal, is transmitted to a central processing unit (CPU) 33, processed to a desired information by a software contained in the CPU 33, and transmitted to a display 40 to be displayed or a printer 40' to be printed out. During the fluorescence detection, the sample 20 is moved by a transport unit 34 in a predetermined mode proper to the sample 20 to obtain information for fluorescence distribution in the sample 20.

FIG. 11 is a schematic view of the most critical region of the laser-induced epifluorescence detection device of the present invention, which focuses fluorescence and scattered light, selects only fluorescence and generates an effective signal. Light emitted from a semiconductor laser 11 as a light source is converted to a circular point about 100 micrometers in diameter or a narrow long elliptical shape about 2 mm long and about 100 micrometers wide by the shape control lens for laser beam, and focused onto a surface of the sample 20. Since the semiconductor laser emits a wavelength varying especially according to temperature and electric current, the excitation filter 41 is used to prevent the wavelength of the incident light from being too close to the wavelength of fluorescence. The excitation filter 41 is an indirect low-pass filter using multiple thin films, and, ideally, must display a step-like sharp cut/pass property at a cut-off wavelength.

The transport unit 34, which is as a sample control means used in the laser-induced epifluorescence detection device of the present invention, transports the sample 20 back and forth, right and left and upward downward, and its composition and structure are well known so that its detailed description is omitted.

FIG. 12 is a block diagram of a system for epifluorescence detection by the small scanner of the present invention. The CPU 33 controls the system, connects with keys by which a user directly enters an order, a position sensor, a transport unit to transport a sample, a memory, a power monitor using an external removable battery power source and displaying remaining time or measurement frequency, and other auxiliary devices including output devices such as a monitor and a printer. By controlling the above-mentioned devices, the CPU 33 functions to control an overall process including light source control, strip transport, detection signal processing, and result presentation and output. These functions may be revised or improved by a software contained in the CPU 33. The software integrates information associated with input items by a user, cartridge type, light source intensity, sample cartridge start and present location, etc., as well as optical detector signal, an this integrated information is properly processed by the CPU 33. In addition, the CPU 33 may temporarily save measurement results of a predetermined frequency by using internal memory capacity, and may establish a function to transmit the stored data to a desired region by using a related protocol with an external communication device.

Figure 13:
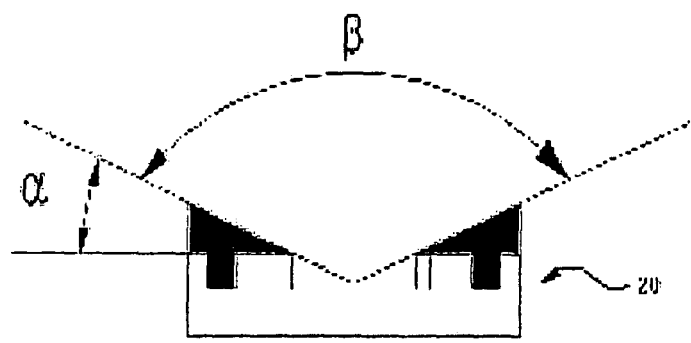
FIG. 13 is a side view showing a state in which a window wall surface of a cartridge housing is inclined to a strip according to the present invention.

FIG. 13 is a sectional view showing a state in which a window wall surface of a cartridge housing is inclined to a strip.

Figure 14:
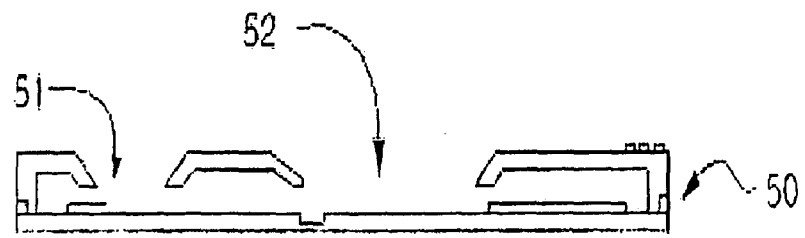
FIG. 14 is a side view showing a cartridge according to the present invention.

Referring FIGS. 13 and 14, the strip shown in FIG. 13 is placed in the cartridge of FIG. 14. For epifluorescence detection, the incident laser light through the window wall surface of the cartridge housing induces the strip to emit fluorescence, and then scattered and reflected. The scattered light acts like noise by being reflected by dust, etc., on a sample surface of the strip according to the depth of the strip in the cartridge and a slope angle ($\alpha$) of the window of the cartridge housing relative to the strip. When a high degree of noise is produced, most light is consumed during the detection process. Thus, in this case, a light source must supply a very bright light, or a sample contained in a strip must emit very abundant fluorescence. For this reason, an additional spatial filter is required to remove noise caused, for example, by the dust present at the surface of the strip. The degree of the noise varies depending on the depth of the strip in the cartridge and the slope angle ($\alpha$) of the window wall surface of the cartridge housing to the strip. Therefore, noise generation can be reduced by properly controlling the slope angle ($\alpha$) of the window wall surface of the cartridge housing to the strip. As shown in the following table, when the slope angle ($\alpha$) of the wall surface of the window of the cartridge housing relative to the strip is 20° or less, the lowest noise generation rate was found, thereby increasing light usage efficiency.

| Slope angle | Noise increase |
|---|---|
| 1°-10° | 10% |
| 20° | 10% |
| 30° | 25% |
| 40° | 30% |

Figure 15:
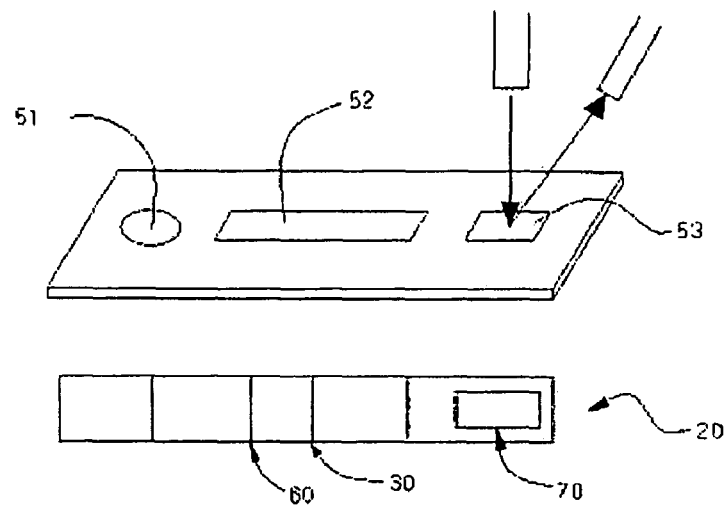
FIG. 15 shows a state of measuring the concentration of an analyte by performing strip reading using a pH paper or an indicator attached to a protein with the passage of a predetermined time after a sample is applied to a strip.
Figure 16:
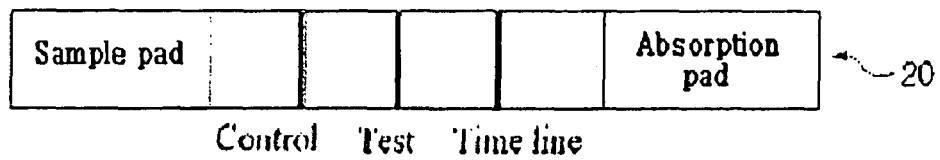
FIG. 16 shows a state of measuring the concentration of an analyte when a detector emits fluorescence upon accumulation after an anti-detector ligand is dispensed in a time control line on a strip.

FIG. 15 shows a state of measuring the concentration of an analyte by performing strip reading using a pH paper or an indicator attached to a protein with the passage of a predetermined time after a sample is applied to a strip. FIG. 16 shows a state of measuring the concentration of an analyte when a detector emits fluorescence upon accumulation after an anti-detector ligand is dispensed in a time control line.

As shown in FIGS. 15 and 16, many kits for quantitative analysis of analytes by employing the principle of the lateral flow quantitative assay technique are problematic in that the lapse of time after sample loading is counted using a timer to indicate a time point of reading without consideration that sample migration is affected by external temperature, humidity, and the like, thereby reducing accuracy of measurement. This problem can be overcome by employing an apparatus sensing the lapse of time after sample loading into a strip or migration of the sample on a membrane and automatically starting strip reading. This apparatus may be designed to have one of the following principles: (1) sensing color change of an indicator according to pH change; or (2) measuring fluorescence intensities from a membrane, sensing their increase with the passage of time and starting reading after a predetermined time.

In case of an apparatus employing the first principle, a pH paper or an indicator attached to a protein is used. When a weak alkali sample contacts an absorption pad, the pH paper or the indicator, which is yellow, is wetted with the sample and changed to red. With the passage of time, the pH paper or the indicator is exposed to larger amounts of the sample solution, and the indicating reagent becomes washed off therefrom, thereby making the pH paper or the indicator white.

For example, color change is checked every twenty seconds.

Example) Yellow→No→Wait→color check again
Red→Yes→Reading White→No→Error (Time over)

In case of an apparatus employing the second principle, an anti-detector ligand is dispensed in a time control line on a membrane. When a detector is accumulated in the time control line, and fluorescence is emitted with intensities higher than a standard level, strip reading is started. In the fluorescence intensities higher than a standard level, the ratio of a fluorescence intensity from the test line to that from the time control line is stabilized. This point is a point to start strip reading. This apparatus scans a time reading window every twenty seconds using a laser to measure fluorescence intensities, and determines whether to start whole strip reading or continue waiting based on the measured fluorescence intensities. Example) measuring fluorescence intensities with the passage of time:

| Time (minute) | Fluorescence intensity of time control line | The ratio of the time control line and test line | remarks |
|---|---|---|---|
| 1 | −100 | −0.2 | |
| 5 | −250 | −0.6 | |
| 10 | −400 | −1.0 | |
| 12 | −500 | −1.2 | ←Reading point |
| 14 | −600 | −1.2 | |

In general, cut-offs of analytes to be analyzed in blood are described in Table 2 (microcystin is an environmental material, existing in water but not in blood).

TABLE 2

| Marker | Unit | Cut-off |
|---|---|---|
| CEA | ng/ml | <5 |
| AFP | ng/ml | <15 |
| PSA | ng/ml | <4 |
| B2M | ng/ml | <2 |
| NSE | ng/ml | <15 |
| CYFRA21-1 | ng/ml | <3.5 |
| Myoglobin | ng/ml | <70 |
| CK-MB | ng/ml | <3 |
| CTnI | ng/ml | <1 |
| CTnT | pg/ml | <60 |
| BNP | pg/ml | <100 |
| microcystin | pg/ml | <300 |

In an additional embodiment according to the present invention, analytes which can be analyzed at a level of pg/ml include those described in Table 3, but are not limited thereto.

| Analytes | Unit | Cut-off |
|---|---|---|
| ACTH | pg/ml | 200-250 |
| Adrenomedullin | pg/ml | 480 ± 135 |
| ANP | pg/ml | 73 |
| Angiotensin II | pg/ml | 21 ± 4 |
| Calcitonin | pg/ml | 10 |
| CNP | pg/ml | 7.36 ± 3.0 |
| Endorphin | pg/ml | 30 ± 5 |
| Gastrin | pg/ml | 26.4 ± 8.4 |
| Ghrelin | pg/ml | 87.79 ± 10.27 |
| NPY | pg/ml | 70.7 ± 5.9 |
| Pancreatic polypeptide | pg/ml | 218 ± 23 |
| Urotensin | pg/ml | 7.70 ± 0.97 |

It has been found that the laser-induced epifluorescence detecting apparatus according to the present invention can assay analytes to a pg/ml level.

Now, the present invention will be described in detail using an embodiment shown in the following examples. However, the examples are for illustration of the present invention and do not limit the scope of the present invention thereto.

Example 1

Preparation of Monoclonal Antibody for Use as Detector and Captor (1) Preparation of Culture Medium Powdered Dulbecco's modified Eagle's media (DMEM) was dissolved in 900 ml of DDW and 3.7 g of sodium bicarbonate was added to the solution to adjust pH to 6.9. The solution was sterilized using a filter having a pore size of 0.45 μm, thus obtaining "incomplete DMEM". 450 ml of the incomplete DMEM was supplemented with 10% bovine calf serum and antibiotic penicillin-streptomycin to obtain "complete DMEM". 5 ml of the complete DMEM was mixed with 5 ml of 100×HT to form HT (hypoxanthine+thymidine) and 5 ml of 100X HAT (hypoxanthine+aminopterin+thymidine) to form HAT medium, respectively.

(2) Preparation and Injection of Antigen

For the first injection, purified enzyme protein solution (50 μg) was mixed with an equal volume (typically 0.3 ml) of complete Freund's adjuvant and the mixture was subjected to sonication for 30 seconds. The resulting solution was injected to BALB/c mice at a dose of 0.4 ml. Three weeks after the first injection, the additional injection was performed to the mice using a solution prepared by mixing the protein solution used for the first injection with incomplete Freund's adjuvant. This booster injection was repeated 2 or 3 times. The final injection was performed using only the protein without any adjuvant 3 to 4 days before a cell fusion experiment. The mice used in the experiment were 6 to 8 weeks old BALB/c, without distinction of sex.

(3) Preparation of Feeder Cells

The feeder cells were prepared 1 to 2 days before the fusion experiment. A mouse, at least 10 weeks old, was sacrificed and the abdominal skin was removed with great care. 5 ml of 11.6% sugar solution was injected intraperitoneally. 1 or 2 minutes later, the injected sugar solution was recovered in an amount of at least 3 ml. The solution was centrifuged (2,000 rpm, 3 minutes) to obtain feeder cells. The feeder cells were suspended in 30 ml of HAT medium and the resulting solution was placed in five 96-well plates, one drop for each well. When the mouse was small, two mice were used to obtain abdominal cells. Also, when contaminating red blood cells were present, the preparation was repeated.

(4) Preparation of Spleen Cells

A mouse immunized with an antigen was sacrificed and its spleen was removed under sterile conditions. The spleen was transferred to a culture dish to which 10 ml of incomplete DMEM had been added in advance and its tissue was disrupted with tweezers, upon which the spleen cells were released to the culture medium. The cells were moved to a 15 ml tube to settle any large or uncrushed tissues for 2 minutes. A 5 ml aliquot from the upper part was centrifuged. The supernatant was removed and the cells were dissolved into 3 ml of incomplete DMEM, which was to be mixed with myeloma cells. For one cell fusion experiment, $3 \times 10^7$ spleen cells were prepared.

(5) Preparation of Myeloma Cells

At 5 days before the cell fusion experiment, SP2/0 Ag14 cells in frozen state were taken out of a liquid nitrogen tank and thawed. The cells were recovered while very slowly adding complete DMEM. Centrifugation was performed to settle the cells, which were resuspended in 10 ml of complete DMEM and passaged at intervals of two days in a $CO_2$ incubator at 37° C. $5 \times 10^7$ myeloma cells were prepared for the cell fusion experiment.

(6) Cell Fusion

The prepared spleen cells and myeloma cells were mixed and centrifuged (2,000 rpm, 3 minutes). The cells were washed once with 20 ml of incomplete DMEM and the supernatant was thoroughly removed. Cell fusion was carried out by grasping the cell vial with hands to maintain a temperature of 37° C. while tapping the lower part of the tube to disrupt the cells. 1 ml of 50% PEG (polyethyleneglycol) solution was added dropwise to the tube over 1 minute and the tube was shaken for 90 seconds to effect the cell fusion. Exactly 2 minutes and 30 seconds after adding the first drop of PEG solution, incomplete DMEM was added to stop the reaction. Here, in order to protect membranes from damage caused by the osmotic pressure shock upon addition of the PEG solution, the addition of incomplete DMEM was carried out by first adding 1 ml over 1 minute, then 2 ml over 1 minute, then 3 ml over 1 minute and so on, until a total 20 ml of incomplete DMEM had been added to the tube. The Cells thus fused were centrifuged and washed with 20 ml of HAT medium to thoroughly remove PEG. The resulting cells were suspended in 65 ml of HAT medium and the resulting solution was added to the 96-well plates, two drops for each well, and cultured in a $CO_2$ incubator at 37° C.

On the third day after the cell fusion, three drops of HT medium were added to each well. The medium of each well was changed at intervals of 3 days and the growth of cells were examined under a microscope. Typically, hybridoma colonies first appeared four days after the fusion and screening of the colonies commenced about 7 days after the fusion. 200l of the medium was transferred to a 24-well plate containing 400 μl of PBS. Cells of wells showing a positive ELISA response were transferred to a new 24-well plate containing 1 ml of HT medium and cultured for an additional 3 to 4 days. After completion of the culturing, 500 μl of the medium was added to a 15 ml tube containing 2 ml of PBS and subjected to a Western blot analysis. Again, cells showing a positive response were transferred to a 6-well plate containing 5 ml of HT medium and cultured. After culturing, the hybridoma cells were flash frozen and cloned by limiting dilution.

(7) Freezing of Hybridoma Cells

Confluent cells grown in a 10 ml culture flask were centrifuged. The settled cells were dissolved in 1 ml of a freezing media containing 90% bovine calf serum, 10% DMSO. The solution was put into a freezer vial, which was placed in a styrofoam box and slowly chilled to −70° C. After two hours, the vial was quickly transferred to a liquid nitrogen tank, in which the cells can be almost permanently preserved.

(8) Limiting Dilution of Hybridoma Cells

Limiting dilution was carried out to select cells capable of producing antibody against an epitope. Firstly, the number of hybridoma cells in log phase growth was calculated using a Neubauer Cell Counter and continuous dilution was performed until 15 cells were contained in 1 ml medium, that is, a drop of medium contained one cell. A drop of the medium was added to each well of the 96-well plate containing the feeder cells, which had been prepared one or two day(s) ago. Every 3 days, the medium was changed. At 5 days, the plate was scanned using an inverted microscope to mark wells where a single colony was observed. At 14 days, hybridoma cells of the marked wells were transferred to a 24-well plate and continuously cultured. After the cultivation, the media were tested by ELISA to identify hybridoma cells producing the desired antibody, which were then stored in a frozen state.

(9) Production of Ascites Fluid

When a large amount of monoclonal antibodies were needed, a BALB/c mouse which had been injected with 500 μl of pristine 9 days before was injected with about $1 \times 10^7$ of the hybridoma cells producing the desired antibody. 10 to 15 days later, the mouse showing proper abdominal distension was anesthetized or killed. Ascitic fluid was harvested using an syringe and centrifuged (4° C., 15,000 rpm, 10 minutes) to remove cells and tissues. The supernatant was divided into portions, which were stored at −70° C. For subsequent experiments, IgG was isolated from the ascitic fluid kept in a frozen state using a Protein A column.

(10) Monoclonal Antibodies for Different Analytes

|  | PSA | Free PSA | AFP | CEA |
|---|---|---|---|---|
| Antigen | Semen | Semen[a] | Amniotic fluid[b] | Human body fluid[c] |
| Captor antibody | 32c5 (IgG2a) | 83c1 (IgG1) | 5c3 (IgG2a) | 34 (IgG1) |
| Detector antibody | 1c1 (IgG2a) | 1c1 (IgG2a) | 20c4 (IgG1) | 17 (IgG2a) |
| Coating buffer solution | Phosphate buffer solution (0.1M, pH 7.4) | Tris buffer solution (0.15M, pH 8.0) | Borax buffer solution (0.2M, pH 8.3) | Carbonate buffer solution (0.5M, pH 9.5) |
| Labeling buffer solution | PBS | PBS | PBS | PBS |

[a]Obtained from Scripps;
[b]Obtained from RDI;
[c]Obtained from Biodesign

Example 2

Preparation of Protein-Fluorescent Material Conjugate

A fluorescent material as a signal generating source was ligated to the mouse monoclonal antibody against an analyte of interest for use in subsequent experiments. Proteins to be used in binding of the fluorescent material were purified to a purity of at least 95%. The proteins were used at a concentration of at least 1 mg/ml for optimal binding. The purified proteins were dialyzed against a buffer solution (0.1 M sodium bicarbonate, pH 8.5) not containing ammonia or amine ions in a refrigerator at 4° C. for 12 to 24 hours in order to facilitate the reaction with the fluorescent material. The proteins dialyzed in the buffer solution were directly but slowly added to powdered Alexa 647 (Molecular Probes, USA) and the reaction was stirred for 1 to 2 hours in a refrigerator at 4° C.

Example 3

Purification of Protein-Fluorescent Material Conjugate

Excess unreacted fluorescent material was removed using a distribution column packed with Sephadex G-25. The purified protein-fluorescent material conjugates were kept in a refrigerator or −20° C. freezer until use.

Example 4

Immobilization of Protein on Nitrocellulose Membrane

The proteins were dispensed on a nitrocellulose membrane in a thin line shape with varying the concentration and amount of protein by means of Bio Dot Dispense connecting injector pump. The membrane with dispensed proteins was stored in a dehumidifier kept at 25° C. and a humidity of 35 to 50% for 2 hours for immobilization. Then, in order to stabilize the protein and prevent non-specific reactions between reagents, the membrane was treated with a stabilizing solution (1% BSA, 0.05% Tween 20, 1% sucrose, 0.1% PVA) and equilibrated for 5 minutes. As the components of the stabilizing solution, BSA may be substituted with gelatin, Tween 20 may be substituted with Triton X-100, sucrose may be substituted with trehalose, PVA (polyvinylalcohol) may be substituted with PEG or PVP (polyvinylpyrrolidone). After removing excess solution the membrane was dried at 40° C. for 30 minutes. The dry membrane was stored in an appropriate container kept at 25° C. and a humidity of 35 to 50% until use.

Example 5

Pretreatment of Sample Pad

The sample pad was pretreated in order to facilitate movement of components of a solution through the nitrocellulose membrane, to maintain a high sensitivity of reaction and to prevent experimental errors due to a non-specific reaction between protein-fluorescent material polymer and a sample.

A sample pad (2.5×30 cm) was sufficiently wetted with a pretreating solution (20 mM Tris-Cl, 0.1% Triton X-100, 0.05% $NaN_3$, pH 8.5) by repeatedly applying 1 ml of the solution and equilibrating for 10 minutes. When whole blood was used as a sample, another pretreating solution (PBS, 10 mM phosphate, 150 mM NaCl, 1% BSA, 0.05% Tween 20, 0.05% $NaN_3$, pH 7.4) was used to prevent hemolysis of red blood cells. After removing excess solution, the sample pad was vacuum dried at a temperature of 50° C. to 60° C. for 1 hour to prevent deformation of the pad. The lyophilization method was selected to minimize denaturation of the protein-fluorescent material conjugate. The prepared sample was stored in an appropriate container under the same conditions as for the foregoing membrane.

Example 6

Preparation of Conjugate Releasing Pad

The protein-fluorescent material conjugates as a detector for an analyte of interest were immobilized upon a pad made of glass fiber, thereby simplifying the assay procedure to a one step process.

The protein-fluorescent material conjugates were diluted 1/1000, 1/500, 1/100 in a buffer solution (PBS, 0.1% gelatin, 0.1% Tween 20, pH 7.4). The general method for applying the mixture to the pad includes soaking a glass fiber pad with the mixture and equilibrating for 5 minutes at room temperature, followed by drying. However, in this example, the mixture was dispensed in an amount of 10, 15, 20 µl/cm using a micro dispenser in order to prevent nonuniform redistribution of the mixture on the surface of the glass fiber pad and to reduce a needed amount of the mixture. The conjugate releasing pad (protein-fluorescent material conjugate pad) can be dried by three methods. The first method was to dry the pad at a temperature below 40° C. for 6 hours, considering stability of the protein component. The second method was to dry the pad in a dehumidifier at room temperature for 16 hours. As the third method, lyophilization may be selected to reduce any chance of the protein component being inactivated, though this method requires more time than the first method. The prepared conjugate releasing pad was stored in an appropriate container under the same conditions as for the foregoing membrane.

Example 7

Dispensation of Protein on NC (Nitrocellulose) Membrane

Each protein to be immobilized on the membrane was diluted in PBS buffer solution to 1 and 2 mg/ml. The solution was dispensed in an amount of 0.88 μl/cm in a line with a width of 0.8 mm on the NC membrane using the Bio Dot dispenser and fixed at RH 35 to 50% for 2 hours. Then, the membrane was treated with a stabilizing solution (1% BSA, 0.05% Tween 20, 0.1% PVA) for stabilization of proteins and prevention of non-specific reactions between reagents, and equilibrated for 5 minutes (As the components of the stabilizing solution, BSA may be substituted with gelatin, Tween 20 may be substituted with Triton X-100, sucrose may be substituted with trehalose, PVA (polyvinylalcohol) may be substituted with PEG or PVP (polyvinylpyrrolidone)). After removing excess solution, the treated membrane was dried at 40° C. for 30 minutes. The resulting dry membrane was assembled with the sample pad, absorption pad, etc. and cut to a width of 4 mm using a cutter so that the final strip had a dimension of 4×60 mm.

Example 8

Quantification of Analyte

Single Test Line

The captor antibody (1 mg/ml) against PSA (prostate specific antigen) to be analyzed was dispensed in the test line region on the NC membrane in an amount of 0.88 μl/cm and rabbit IgG (1 mg/ml, 0.1 mg/ml, 0.05 mg/ml, 0.01 mg/ml) was dispensed on the reference line in an amount of 0.88 μl/cm. The resulting membrane was stored at RH of 35 to 50% for 2 hours for immobilization. Then, the membrane was treated with a stabilizing solution (1% BSA, 0.05% Tween 20, 0.1% PVA) for stabilization of proteins and prevention of non-specific reactions between reagents, and equilibrated for 5 minutes. After removing excess solution, the treated membrane was dried at 40° C. for 30 minutes. The material to react with the protein to be analyzed via antigen-antibody reaction was fluorescently-labeled with Alexa 647. The protein-fluorescent material conjugates were diluted 1/100 in a dilution buffer solution (PBS, 0.1% gelatin, 0.1% Tween 20, pH 7.4). 5% trehalose as a stabilizing agent was added to the diluted solution. The solution was then dispensed in an amount of 20 μl/cm on the surface of glass fiber using a dispenser, followed by lyophilizing.

The prepared NC membrane, conjugate releasing pad, sample pad and absorption pad were adhered to the backing and assembled in a plastic housing. The PSA standard solution was diluted in a dilution buffer solution (PBST, 10 mM phosphate, 150 mM NaCl, 0.3% Tween 20, pH 7.4) to 0, 4, 8, 16 and 32 ng/ml. The concentrations of the prepared standard solutions were confirmed using a PSA ELISA kit. For proteins dispensed on the reference line, each standard solution as prepared above was dropped in a specimen input hole of the assay kit and 10 minutes later, the kit was placed in the laser-induced epifluorescence detecting apparatus according to the present invention. The apparatus is designed to express an amount of fluorescence of the detector/analyte/captor conjugates accumulated on a test line or reference line as a peak and display the amount on a monitor. The amount of the Rabbit IgG showing a peak similar to 8 ng/ml PSA was determined as the amount to be dispensed on the reference line. After determining the concentration of the reference line, respective PSA standard solutions were applied to the assay kits while following the same method as described above. 10 minutes later, the apparatus displayed the numerical value of fluorescence intensity of the analyte which was calculated by inputting a ratio of the fluorescence intensities of the test line and the reference line into an analogized equation by the polynomial regression method, to obtain the numerical value of the fluorescence intensity of the analyte.

Example 9

Quantitative Analysis of Total/Free PSA

Figure 19:
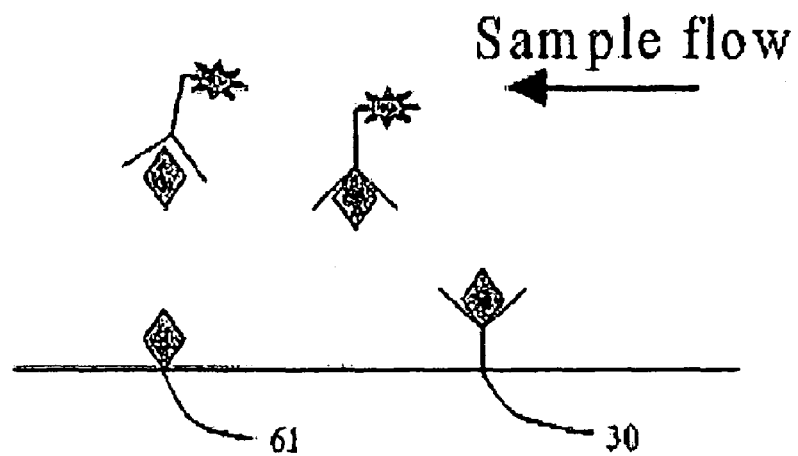
FIG. 19 shows a sample flow of the strip in case of fixing an Ag line with which Ag or a detector reacts in back of the test line and the amount of Ag is excessive at a state of being mixed with a detector.
Figure 20:
FIG. 20 is a graph showing signal variation shown in FIG. 19.

A monoclonal antibody (1 mg/ml) specifically reacting with total PSA and free PSA were dispensed on the NC membrane in an amount of 0.88 μl/cm. Separately, a monoclonal antibody having an epitope different from that of the capture antibody was bound to a fluorescent material, Alexa 647, to form an antibody/fluorescent material conjugate. This conjugate was mixed with a PBS buffer solution containing 5% trehalose, 1% gelatine as a stabilizer to obtain a 1/100 dilution. A glass fiber pad was impregnated with the dilution in an amount of 50 μl/cm$^2$, and lyophilized to obtain a antibody/fluorescent material conjugate pad. The PSA standard solution was diluted with a dilution buffer solution (PBST, 10 mM phosphate, 150 mM NaCl, 0.3% Tween 20, pH 7.4) to 0, 4, 8, 16 and 32 ng/ml. The concentrations of the prepared standard solutions were confirmed using a PSA ELISA kit. Each standard solution as prepared above was dropped in a specimen input hole of the assay kit and 15 minutes later, each test zone (two zones for total PSA and free PSA) was examined for fluorescence intensity using the laser-induced epifluorescence detecting apparatus according to the present invention. In case of an actual specimen such as serum or whole blood, a concentration of the specimen was determined using a PSA ELISA kit before the specimen was applied to the assay strip. The results are shown in FIG. 19 and FIG. 20.

Example 10

Quantitative Analysis of AFP, CEA, CA15-3, CA19-9 and CA125 Specific Antigens

Multiple Test Lines

Three or more of monoclonal antibodies (1 mg/ml) each of which specifically reacts with α-feto protein (AFP, a liver cancer marker), carcinoembryonic antigen (CEA, a tumor marker for various cancer, mainly used for colon cancer), CA15-3, CA19-9 and CA125 were dispensed in thin lines and immobilized on a nitrocellulose membrane. Monoclonal antibodies having an antigenic determinant different from that of the immobilized capture antibodies were individually labeled with a fluorescent material to provide antibody-fluorescent material conjugates as detectors. These antibody-fluorescent material conjugates were individually diluted to 100 times, thus yielding detection buffers. Reference solutions were prepared by diluting reference materials to be analyzed with a dilution buffer (PBST, 10 mM phosphate, 150 mM NaCl, 0.3% Tween-20, pH 7.4) with appropriate concentration ranges containing a clinically important cut-off value for each analyte. The prepared reference solutions were confirmed using an ELISA kit. Each reference solution and each detection buffer were applied along to a test strip through a sample loading inlet. After 15 min, the test strip was scanned by a fluorescence analyzer, and intensities of fluorescence from the respective test lines were compared with those from the reference line to quantify each analyte.

Figure 24:
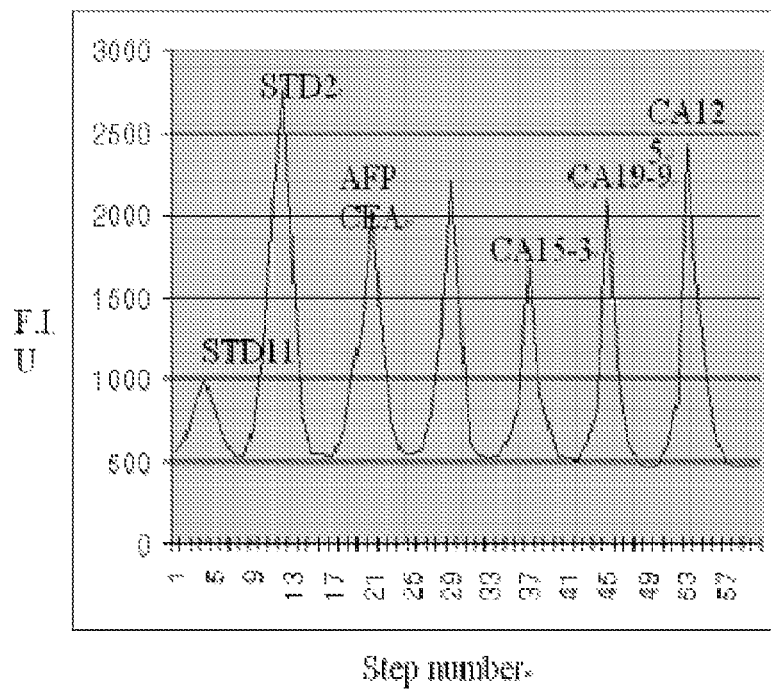
FIG. 24 is a graph showing quantitative analysis of AFP, CEA, CA15-3, CA19-9 and CA125 specific antigens.

As an embodiment of this method, AFP, CEA, CA15-3, CA19-9 and CA125 were analyzed by fluorescence immunochromatography, as follows. First, mouse IgG was immobilized in double reference lines on a developing membrane, capture antibodies to AFP, CEA, CA15-3, CA19-9 and CA125 were dispensed sequentially in test lines in back of the reference lines at regular intervals and immobilized. The specific antigens contained in a specimen were detected by the detection buffers individually containing the detector antibodies and a fluorescence analyzer. As shown in FIG. 24, the capture antibodies and the detector antibodies were found to specifically recognize the antigens. Fluorescence Intensities were detected in a concentration-dependent manner.

Example 11

Preparation of Fluorescently-Labeled Antigen or Antibody

Various types of fluorescent material were bound to antibodies and antigens for comparison. FITC (fluorescein-isothiocyanate), rhodamine, Alexa series, Cy3, Cy5 (Molecular probes, Inc.) were used as fluorescent materials in this examples. In the experiment, Alexa series, Cy3 and Cy5 showed excellent results in stability and reproducibility. In the subsequent experiments, Alexa 647 was used as a fluorescent material. The prepared fluorescent material/antigen (antibody) conjugate showed a stable reactivity and could be used for a sufficiently long period of time without decoloration.

Example 12

Determination of Concentrations of Protein-Fluorescent Material Conjugate and Immobilized Protein on NC Membrane In order to determine optimum concentrations of a detector and a capture protein needed to detect an analyte, serial dilution was performed. Various amounts of a capture protein were immobilized on a NC membrane. Serial dilutions of a protein-fluorescent material conjugate were prepared. A standard solution of each analyte was mixed with the dilutions of the protein-fluorescent material conjugate and the mixture solution was applied to a test strip. After the development of the solution was completed, the test strip was assayed using the laser-induced epifluorescence detecting apparatus according to the present invention. The concentration of the immobilized protein was 1, 1.2, 1.4, 1.6, 1.8 and 2 mg/ml for each measurement item and the dispensed amount of the protein was 0.88 µl/cm. At a given concentration of the capture protein, when the concentration of the protein-fluorescent material conjugate was increased or decreased, the fluorescence intensity of the analyte at the same concentration was also increased or decreased. Additionally, at a given concentration of the protein-fluorescent material conjugate, when the concentration of the capture protein was changed, the same result as above was obtained. In both experiments, when the concentration exceeds a certain limit, non-specific reactions increased. By putting the above results together, the optimum concentrations of reagents which can lower the detection limit of an analyte and minimize non-specific reactions between the sample and the capture or the detector was determined.

Example 13

Minimum Detection Limit of Analyte and Linearity

The PSA monoclonal antibody of the optimum concentration determined in Example 12 was dispensed at amount of 0.88 µl/cm on a NC membrane. The antibody-fluorescent material conjugate diluted to the concentration determined in Example 12 was mixed with a dilution buffer solution (PBS containing 5% trehalose, 1% gelatine, pH 7.4). The resulting dilution was dispensed to a glass fiber pad in an amount of 20 µl/cm, followed by lyophilization, to obtain a antibody-fluorescent material conjugate pad. Then, the PSA standard solutions at a concentration in a range of 1 mg/ml to 1 pg/ml were applied to the strip to determine the minimum detection limit of the analyte and the linearity range of the assay kit using the epifluorescence analyser. As shown in FIG. 14, the minimum detection limit of PSA was 10 pg/ml and the linearity range was considerably wide, from 10 pg/ml to 1 µg/ml. AFP, CEA, CRP of Example 10 also showed minimum detection limits much lower than the cut-offs required for diagnosis.

Example 14

In this example, for comparison, a fluorescence intensity of a fluorescent material was measured using the laser-induced epifluorescence detecting apparatus according to the present invention and a conventional laser-induced fluorescence detecting scanner, Scan Life, produced by GSI.

Serial dilutions of PSA as an analyte were prepared and mixed with the protein-fluorescent material. The mixture solution was applied to a strip as in Example 7. The result was imaged using the conventional scanner. Also, a lateral flow assay strip prepared using the same method and conditions was imaged using the laser-induced epifluorescence detecting apparatus according to the present invention. The imaged data were converted into numerical data using a related program. The results are shown in FIG. 15. From the results of FIG. 15, it was noted that both the laser-induced epifluorescence detecting apparatus according to the present invention and the conventional fluorescence detecting scanner showed a fluorescence intensity increasing according to the concentration of the analyte, while the fluorescence intensity measured by the laser-induced epifluorescence detecting apparatus according to the present invention was much higher than that measured by the conventional fluorescence detecting scanner.

Example 15

Determination of Location of Reference Line

In order to determine the location of a reference line on a strip, a strip having a reference line in front of a test line was prepared. Mouse IgG was immobilized in front of a test line in which an anti-AFP antibody has been immobilized. The concentration of AFP contained in a sample was measured several times using detection buffers containing fluorescently labeled anti-mouse IgG and the anti-AFP antibody. The resulting CV values were compared with the case of immobilizing mouse IgG in back of the test line. In addition, rabbit IgG and avidin were immobilized in reference lines and compared with each other under the same conditions as described above. The results are given in the following table.

Comparison of CV values for CRP concentration according to immobilization location of reference materials

|  | Reference material | | | | | |
| --- | --- | --- | --- | --- | --- | --- |
|  | Mouse IgG | | Rabbit IgG Location of reference line for test line | | Avidin | |
|  | Front | Back | Front | Back | Front | Back |
| CV value (%) | 5 | 8.5 | 9.2 | 10 | 10 | 13.7 |

As shown in the above table, when the mouse IgG reference material was immobilized in front of the test line, the lowest CV value for AFP concentration was found. Therefore, this case provides excellent reproducibility in AFP concentration.

Example 16

Figure 18:
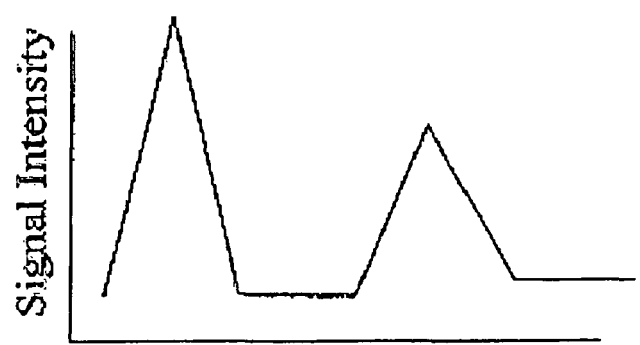
FIG. 18 is a graph showing signal variation shown in FIG. 17.

Dispensation of Ag Line with which Ag or Detector Reacts in Back of the Viewing Window The hook effect occurs when silver (Ag) is present in excessive amounts, and brings about false negative results that cause fatal wrong diagnosis. A method of quantifying silver by inducing binding of a capture antibody to a detector and silver in a mixture like the present system has a potential of causing the hook effect and thus errors in quantitative assay. In a normal case, when an excessive detector binds to both free silver and silver immobilized in an Ag line, signals are generated. As shown in FIGS. 18 and 20, signals increase according to the increased concentration of Ag in the test line 30, whereas, in the Ag line 61, signals decrease according to the increased concentration of Ag because free detectors are exhausted in a high concentration of Ag.

When Ag in a mixture with a detector is present in excessive amounts, the free form of the detector is exhausted. Thus, in this case, signals are not generated in an Ag line or capture line. Therefore, this case is distinguishable from a case of using a detector at a state of being not mixed with Ag, in which a signal variation in the Ag line can be calculated according to the amount of consumed free detectors, thereby extending a detection range of a related system.

Figure 21:
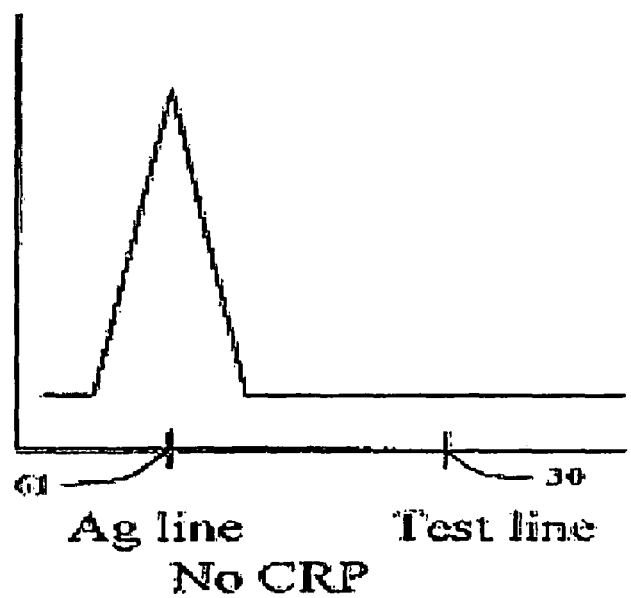
FIG. 21 is a graph showing signal variation when Catabolite Regulatory Protein (CRT) is not used as an analyte.
Figure 22:
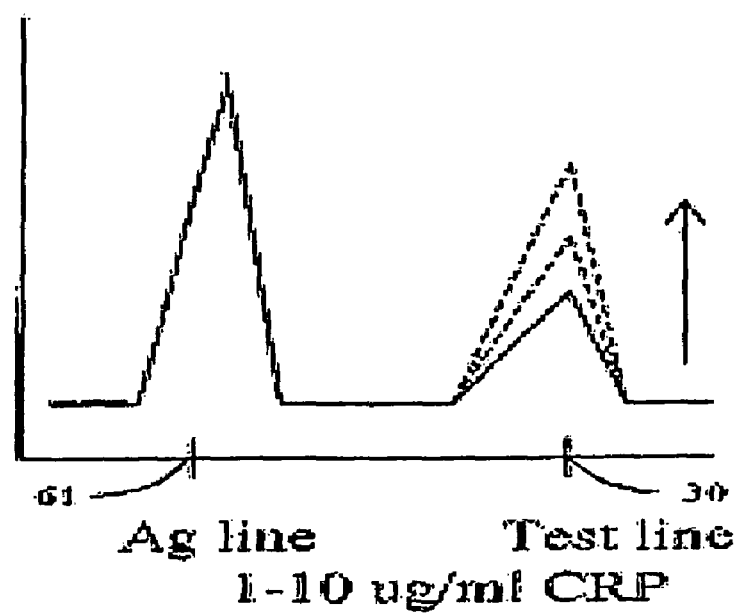
FIG. 22 is a graph showing signal variation when Catabolite Regulatory Protein (CRT) is used 1-10 μg/ml as an analyte.
Figure 23:
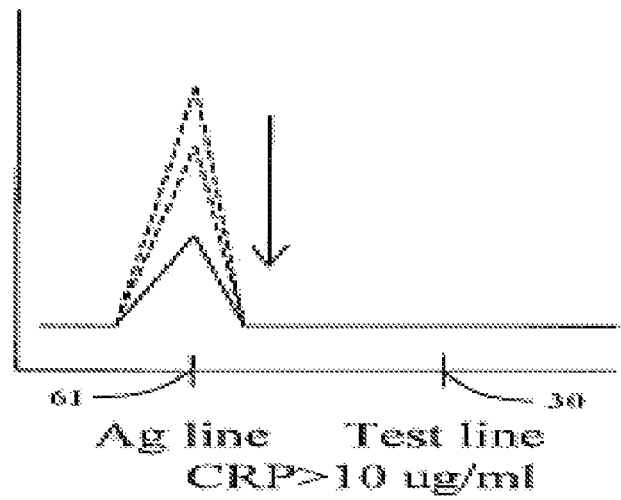
FIG. 23 is a graph showing signal variation when Catabolite Regulatory Protein (CRT) is used more than 10 μg/ml as an anslyte.

Test results using Catabolite Regulatory Protein (CRP) as an analyte are given FIGS. 21 to 23.

As shown in FIGS. 21 to 23, location of the Ag line 61 in back of the test line 30 extends the detection range of a related system.

Example 17

Dispensation of Avidin Protein on NC (Nitrocellulose) Membrane

Avidin to be immobilized was diluted in PBS buffer solution to 1 or 2 mg/ml. The solution was dispensed in an amount of 0.88 µl/cm as a line with a width of 0.8 mm on the NC membrane using the Bio Dot dispenser and fixed at RH 35 to 50% for 2 hours. Then, the membrane was treated with a stabilizing solution (1% BSA, 0.05% Tween 20, 0.1% PVA) for stabilization of proteins and prevention of non-specific reactions between reagents, and equilibrated for 5 minutes (As the components of the stabilizing solution, BSA may be substituted with gelatin, Tween 20 may be substituted with Triton X-100, sucrose may be substituted with trehalose, PVA (polyvinylalcohol) may be substituted with PEG or PVP (polyvinylpyrrolidone)). After removing excess solution, the treated membrane was dried at 40° C. for 30 minutes. The resulting dry membrane was assembled with the sample pad, absorption pad, etc. and cut to a width of 4 mm using a cutter so that the final strip had a dimension of 4×60 mm.

Example 18

Quantification of Analyte Using Avidin-Biotin (Single Test Line)

The avidin (1 mg/ml) and rabbit IgG (1 mg/ml) were dispensed in the test line region and reference line in an amount of 0.88 µl/cm over the NC membrane. The resulting membrane was stored at RH of 35 to 50% for 2 hours for immobilization. Then, the membrane was treated with a stabilizing solution (1% BSA, 0.05% Tween 20, 0.1% PVA) for stabilization of proteins and prevention of non-specific reactions between reagents, and equilibrated for 5 minutes. After removing excess solution, the treated membrane was dried at 40° C. for 30 minutes. The material to react with the protein to be analyzed via antigen-antibody reaction was fluorescently-labeled with Alexa 647. The protein to capture the analyte was coupled with biotin. Also, the antibody to bind to the protein dispensed on the reference line via antigen-antibody reaction was fluorescently-labeled with Alexa 647. The protein-fluorescent material conjugate and the protein-biotin conjugate were diluted 1/100 in a dilution buffer solution (PBS, 0.1% gelatin, 0.1% Tween 20, pH 7.4).

The prepared NC membrane, sample pad and absorption pad were adhered to the backing, cut to a dimension of 4×60 mm and assembled in a plastic housing. The PSA standard solution was diluted in a dilution buffer solution (PBST, 10 mM phosphate, 150 mm NaCl, 0.3% Tween 20, pH 7.4) to 0, 4, 8, 20 and 40 ng/ml. The concentrations of the prepared standard solutions were confirmed using a PSA ELISA kit. Each of the prepared PSA standard solutions, protein-Alexa 647 conjugate and protein-biotin conjugate, and the protein-Alexa 647 capable of recognizing the protein dispensed on the reference line, were dropped in a specimen input hole of the assay kit and 10 minutes later, the kit was placed in the laser-induced epifluorescence detecting apparatus according to the present invention. The apparatus was designed to display the fluorescence intensity of the detector/analyte/capture conjugate accumulated on the test line and fluorescence intensity of protein-fluorescent material conjugate on the reference line as peaks on a monitor. Also, the apparatus displayed the numerical value of fluorescence intensity of the analyte which was calculated by inputting a ratio of the fluorescence intensities of the test line and the reference line into an analogized equation by the polynomial regression method, to obtain the numerical value of the fluorescence intensity of the analyte. The results are noted that greater sensitivity and reproducibility can be obtained by using avidin-biotin.

INDUSTRIAL APPLICABILITY

As described hereinbefore, the present invention provides a lateral flow quantitative assay method. The present assay method is advantageous in terms of allowing quantitative point-of-care diagnostics in hospitals, being capable of specifically detecting a disease marker by optimizing a lateral flow assay biochip for diagnosis of a specific disease, allowing more accurate quantitative analysis of analytes, and being capable of simultaneously analyzing several cancer markers, reducing the hook effect and widening detection range and accurately measuring concentration of analytes. In addition, the present invention provides a strip, a laser-induced epifluorescence detection device and a small scanner for the method.

The invention claimed is:

1. A lateral flow quantitative assay method comprising:

applying a liquid sample that is expected to contain an analyte to one end of a chromatography medium;

migrating the liquid sample through the chromatography medium to react the analyte with a labeled detector adsorbed on a section located at a predetermined distance from the sample application site in a sample developed direction, thereby forming an analyte-labeled detector conjugate;

migrating the analyte-labeled detector conjugate through the chromatography medium to react the analyte-labeled detector conjugate with an unlabeled captor that is identical to or different from the labeled detector and immobilized on a viewing window defined around a middle portion of the chromatography medium, thereby forming a labeled detector-analyte-unlabeled captor triple conjugate in which the analyte is captured between the labeled detector and the unlabeled captor in a sandwich-like fashion; and measuring an amount of the triple conjugate to quantify the analyte in the liquid sample, wherein the method is characterized in that:

(a) the labeled detector is labeled with a fluorescent substance and reacts with the analyte in the liquid sample to form the fluorescently-labeled detector-analyte conjugate;

(b) the unlabeled captor is dispensed in lines within a viewing window on the chromatography medium and reacts with the fluorescently-labeled detector-analyte conjugate that has been migrated along the chromatography medium to form the fluorescently-labeled detector-analyte-unlabeled captor triple conjugate;

(c) a reference detector, which is different from the detector and the captor and labeled with a fluorescent material identical to that used in labeling the detector and reacts with a reference material in the liquid sample, is adsorbed on the section of the chromatography medium where the fluorescently-labeled detector is adsorbed, and an unlabeled reference captor that reacts with the fluorescently-labeled reference detector is dispensed and immobilized in double reference lines in front of the viewing window on the chromatography medium to provide a reference conjugate of fluorescently-labeled reference detector-reference material-unlabeled reference captor as the liquid sample passes through the chromatography medium; and (d) an amount of the analytes is determined by passing a laser presented from a shape control lens for laser beam through an exciter filter, irradiating the filtered light to the epifluorescence medium containing the triple analyte conjugate and the reference conjugate, passing light reflected from the epifluorescence medium through a collection lens to form parallel light, passing the parallel light through a fluorescent filter to remove scattered incident light and presenting only a pure fluorescence component to a condenser lens to focus the pure fluorescence component to a center of a pinhole, removing light except for the parallel light at the pinhole, presenting the parallel light to an optical detector, transmitting the incident parallel light to a CPU via an analog digital converter (ADC), and comparing a fluorescence intensity of the triple analyte conjugate with a reference fluorescence intensity of the reference conjugate to quantify the analyte.

2. The lateral flow quantitative assay method as set forth in claim 1, being characterized in that an Ag line with which Ag or a detector reacts is further immobilized in back of the viewing window to extend signal detection range by calculating a signal variation of the Ag line.

3. The lateral flow quantitative assay method as set forth in claim 1, wherein the unlabeled reference captor is mouse IgG.

4. The lateral flow quantitative assay method as set forth in claim 1, wherein the detector is used in a number of three to five, and the captor is selected from among α-feto protein (AFP), carcinoembryonic antigen (CEA), CA15-3, CA19-9 and CA125 in an identical number to the number of the detector and dispensed and immobilized in identical lines to those of the captor within the viewing window, thereby allowing simultaneous quantitative analysis of three to five analytes.

5. A lateral flow quantitative assay strip, comprising:

a backing;

a sample pad adhered to one end of the backing and to which a liquid sample is applied;

a conjugate releasing pad adhered to the backing in such a way that one end of the sample pad, close to an opposite end of the backing, overlaps with an end of the conjugate releasing pad to which a labeled detector is releasably attached to react with an analyte in the liquid sample to form a conjugate;

a chromatography medium adhered to the backing in such a way that one end of the medium overlaps with an end of the conjugate releasing pad, close to an opposite end of the backing, and on which a captor is immobilized, which is identical to or different from the labeled detector and reacts with and captures a conjugate released from the conjugate releasing pad as the sample develops to form a sandwich type conjugate; and an absorption pad to absorb the sample developing along the chromatography medium and to absorb and remove unreacted labeled substances, wherein the strip is characterized in that:

the labeled detector releasably attached to the conjugate releasing pad is labeled with a fluorescent material;

a reference detector that is labeled with a fluorescent material identical to that used in labeling the labeled detector and reacts with a reference material in the liquid sample is further releasably attached to the conjugate releasing pad;

the captor is dispensed and immobilized in lines within a viewing window on the chromatography medium, and an unlabeled reference captor that is different from the detector and the captor is dispensed and immobilized in double reference lines in front of the viewing window on the chromatography medium, to form a conjugate of fluorescently-labeled detector-analyte-unlabeled captor and a reference conjugate of fluorescently-labeled reference detector/reference material-unlabeled reference captor as the liquid sample passes through the chromatography medium; and an amount of the analyte is determined by passing a laser presented from a laser beam shape control lens through an exciter filter, irradiating the filtered light to the epifluorescence medium containing the triple analyte conjugate and the reference conjugate, passing light reflected from the epifluorescence medium through a collection lens to form parallel light, passing the parallel light through a fluorescent filter to remove scattered incident light and presenting only a pure fluorescence component to a condenser lens to focus the pure fluorescence component to a center of a pinhole, removing light except for the parallel light at the pinhole, presenting the parallel light to an optical detector, transmitting the incident parallel light to a CPU via an analog digital converter (ADC), and comparing a fluorescence intensity of the triple analyte conjugate with a reference fluorescence intensity of the reference conjugate to quantify the analyte.

6. The lateral flow quantitative assay strip as set forth in claim 5, being characterized in that an Ag line with which Ag or a detector reacts is further dispensed and immobilized in back of the viewing window to extend signal detection range by calculating a signal variation of the Ag line.

7. The lateral flow quantitative assay strip as set forth in claim 5, wherein the unlabeled reference captor is mouse IgG.

8. The lateral flow quantitative assay strip as set forth in claim 5, wherein the detector is used in a number of three to five, and the captor is selected from among α-feto protein (AFP), carcinoembryonic antigen (CEA), CA15-3, CA19-9 and CA125 in an identical number to the number of the detector and dispensed and immobilized in identical lines to those of the captor within the viewing window, thereby allowing simultaneous quantitative analysis of three to five analytes.

9. A small scanner for quantitative analysis of an analyte, which is integrated with a laser-induced epifluorescence detection device into a single body,
wherein the laser-induced epifluorescence detection device comprises:
(i) a strip, comprising:
a backing;
a sample pad adhered to one end of the backing and to which a liquid sample is applied;
a conjugate releasing pad adhered to the backing in such a way that one end of the sample pad, close to an opposite end of the backing, overlaps with an end of the conjugate releasing pad to which a labeled detector is releasably attached to react with an analyte in the liquid sample to form a conjugate;
a chromatography medium adhered to the backing in such a way that one end of the medium overlaps with an end of the conjugate releasing pad, close to an opposite end of the backing, and on which a captor is immobilized, which is identical to or different from the detector and reacts with and captures a conjugate released from the conjugate releasing pad as the sample develops to form a sandwich type conjugate; and
an absorption pad to absorb the sample developing along the chromatography medium and to absorb and remove unreacted labeled substances,
wherein the strip is characterized in that:
the detector releasably attached to the conjugate releasing pad is labeled with a fluorescent material;
a reference detector that is labeled with a fluorescent material identical to that used in labeling the detector and reacts with a reference material in the liquid sample is further releasably attached to the conjugate releasing pad;
the captor is dispensed and immobilized in lines within a viewing window on the chromatography medium; and
an unlabeled reference captor that is different from the detector and the captor is dispensed and immobilized in double reference lines in front of the viewing window on the chromatography medium;
(ii) a cartridge to install therein the strip, the cartridge including a sample loading inlet and a window having a sloped wall surface, which are formed on a top plate of a cartridge housing; and
(iii) a laser, a shape control lens for laser beam, an exciter filter, a collection lens, a fluorescent filter, a condenser lens, a spatial filter, an optical detector, an analog digital converter (ADC) and a CPU,
wherein the components of the detection device are arranged in a structure such that a laser presented from a lens for control of shape of a laser beam of the laser is passed through an exciter filter, the filtered light is irradiated to an epifluorescence medium containing a conjugate of fluorescently-labeled detector-analyte-unlabeled captor and formed in the viewing window and a reference conjugate of fluorescently-labeled reference detector-reference material-unlabeled reference captor formed in the reference line as the liquid sample passes through the chromatography medium of the strip, light reflected from the epifluorescence medium is passed through a collection lens to form parallel light, the parallel light is passed through a fluorescent filter to remove scattered incident light, only a pure fluorescence component is presented to a condenser lens to focus the pure fluorescence component to a center of a pinhole, light except for the parallel light is removed at the pinhole, the parallel light is presented to an optical detector, and the incident parallel light is transmitted to CPU via an analog digital converter (ADC),
wherein the small scanner allows the detection device to determine an amount of the analyte in the sample by comparing a fluorescence intensity of the triple analyte conjugate with a reference fluorescence intensity of the reference conjugate.

10. The small scanner as set forth in claim 9, wherein the unlabeled reference captor is mouse IgG.

11. The small scanner as set forth in claim 9, wherein the detector is used in a number of three to five, and the captor is selected from among α-feto protein (AFP), carcinoembryonic antigen (CEA), CA15-3, CA19-9 and CA125 in an identical number to the number of the detector and dispensed and immobilized in identical lines to those of the captor within the viewing window, thereby allowing simultaneous quantitative analysis of three to five analytes.

12. The small scanner as set forth in claim 9, wherein the window wall surface of the cartridge housing has a slope angle of 20° or less relative to the strip.

13. The small scanner as set forth in claim 9, being characterized in that an Ag line with which Ag or a detector reacts is further dispensed and immobilized in back of the viewing window to extend a signal detection range by calculating a signal variation of the Ag line.

14. The small scanner as set forth in claim 9, wherein the cartridge further includes a time reading window on the top plate of the cartridge housing, and a pH paper or an indicator attached to a protein is attached onto the strip, to determine whether to start strip reading by the time reading window color by detecting change of the pH paper or the indicator when a sample is loaded through the sample loading inlet and contacts the absorption pad.

15. The small scanner as set forth in claim 9, wherein the cartridge further includes a time reading window on the top plate of the cartridge housing, and an anti-detector ligand is further dispensed in a time control line on a strip, to determine whether to start strip reading by time reading window by measuring intensities of fluorescence emitted from the detector accumulated in the time control line by the laser-induced epifluorescence detection device.

* * * * *